(12) United States Patent
Healey et al.

(10) Patent No.: US 8,288,398 B2
(45) Date of Patent: Oct. 16, 2012

(54) ANTIPROLIFERATIVE PYRIMIDYL, FUSED PYRIMIDYL AND PYRIMIDYL HYDRAZONES

(75) Inventors: Brian Healey, Scituate, MA (US); Zhong Zhao, Wayland, MA (US); Amanda Sutton, Hingham, MA (US); Matthias Schwarz, Gland (CH)

(73) Assignee: Merck Serono SA, Coinsins, Vaud (CH)

( * ) Notice: Subject to any disclaimer, the term of this patent is extended or adjusted under 35 U.S.C. 154(b) by 1165 days.

(21) Appl. No.: 12/096,110

(22) PCT Filed: Dec. 8, 2006

(86) PCT No.: PCT/EP2006/069460
§ 371 (c)(1),
(2), (4) Date: Jun. 4, 2008

(87) PCT Pub. No.: WO2007/065940
PCT Pub. Date: Jun. 14, 2007

(65) Prior Publication Data
US 2008/0287474 A1 Nov. 20, 2008

Related U.S. Application Data

(60) Provisional application No. 60/748,575, filed on Dec. 8, 2005.

(30) Foreign Application Priority Data

Mar. 14, 2006 (EP) ..................................... 06111071

(51) Int. Cl.
*A01N 43/54* (2006.01)
*A61K 31/517* (2006.01)

(52) U.S. Cl. ..................................... 514/266.4; 544/293
(58) Field of Classification Search .................. 544/293, 544/333, 283, 242
See application file for complete search history.

(56) References Cited

U.S. PATENT DOCUMENTS

| 6,503,914 | B1 * | 1/2003 | Benish et al. | 514/260.1 |
| 2004/0253632 | A1 * | 12/2004 | Rhode et al. | 435/7.1 |
| 2006/0122178 | A1 * | 6/2006 | Cottam et al. | 514/232.5 |

FOREIGN PATENT DOCUMENTS

| JP | 34003376 | * | 5/1959 |
| WO | WO 02/057271 | | 7/2002 |
| WO | WO 03047516 A2 | * | 6/2003 |
| WO | WO 03075828 A2 | * | 9/2003 |
| WO | WO 2006/029850 | | 3/2006 |
| WO | WO 2006/053109 | | 5/2006 |

OTHER PUBLICATIONS

N.O. Nesterova et al., Farmatsevtichnii Zhurnal (Kiev), 1, 5-10 (2004).*
S. Asano et al., Yakugaku Zasshi, 78, 450-4 (1958).*
T.D. Duffy et al., Journal of the Chemical Society, Perkin Transactions 1, 16, 1921-1929 (1974).*
S. Jantova et al., Folia Biologica (Prague), 43(2), 83-89 (1997).*
N.O. Nesterova et al., 1 Farmatsevtichnii Zhurnal (Kiev), 5-10 (2004).*
G.L. Bundy et al., 37 Journal of Heterocyclic Chemistry 1471-1476 (2000).*
Giner-Sorolla, A. et al. "Nitrosaminopurines and Nucleosides, Synthesis and Biological Activity" *Journal of Medicinal Chemistry*, 1973, XP-002394944, pp. 365-369, vol. 16, No. 4.
Barchechath, S. D. et al. "Inhibitors of Apoptosis in Lymphoctes: Synthesis and Biological Evaluation of Compounds Related to Pifithrin-α" *J. Med. Chem.*, 2005, XP-002394943, pp. 6409-6422, vol. 48.
El-Kerdawy, M. M. et al. "A Convenient Synthesis of 3-Aryl-1,2,4-triazolo [4,3-c] quinazolines" *J. Heterocyclic Chem.*, 1990, XP-002394947, pp. 497-501, vol. 27, No. 3.
Chemical Abstracts, Yakugaku Zasshi, Nov. 10, 1958, XP-002394942, p. 18428B, vol. 52, No. 21, Abstract only.
Hegarty, A. F. et al. "A Change from Rate-determining Bromination to Geometric Isomerisation of Pyridylhydrazones" *Journal of the Chemical Society*, 1973, XP002394945, pp. 1466-1471.
Pellerano, C. et al. "Sistemi chelanti tridentate N-N-N quali potenziali agenti antitumorali", *Farmaco, Edizione Scientifica*, 1985, XP-001013543, pp. 645-654, vol. 40, No. 9.
Godefroy, L. et al. "Etude de la chloro-4-pyrido-[3.2-d] pyrimidine et des hydrazine-4-pyrido-[3.2-d] et [2,3-d]pyrimidines" *Comptes-Rendus Des Sceances Hebdomadaires De L'Academie Des Sciences, Section C*, Oct. 22, 1973, pp. 703-706, vol. 277.

\* cited by examiner

*Primary Examiner* — James O. Wilson
*Assistant Examiner* — Alexander R Pagano
(74) *Attorney, Agent, or Firm* — Saliwanchik, Lloyd & Eisenschenk

(57) ABSTRACT

The present invention is related to a novel series of pyrimidyl or fused pyrimidyl hydrazones. Compounds of Formula (I) wherein A is selected from the group consisting of Formulas (A1), (A2), (A3), (A4), (A5) are useful for the treatment and/or prevention of a proliferative disease.

2 Claims, No Drawings

ANTIPROLIFERATIVE PYRIMIDYL, FUSED PYRIMIDYL AND PYRIMIDYL HYDRAZONES

Cross-Reference to Related Application

This application is the U.S. national stage application of International Patent Application No. PCT/EP2006/069460, filed Dec. 8, 2006, which claims the benefit of U.S. Provisional Patent Application No. 60/748,575, filed Dec. 8, 2005.

FIELD OF THE INVENTION

The present invention relates to pyrimidyl and fused pyrimidyl hydrazones, methods of treatment and pharmaceutical compositions that utilize or comprise one or more of such compounds. The compounds of the invention are useful for the treatment and/or prevention of proliferative diseases.

BACKGROUND OF THE INVENTION

Biologically active molecules that interact specifically with certain proteins or interfere with signalling pathways have tremendous value not only for the functional analysis of genes but also for drug development. Drug development is more and more influenced by new screening techniques to find biological active molecules. In forward chemical genetic screening approaches targets are not specified a priori. However, screening against the entire pathway eliminates any bias about what might score in the screen. Forward chemical genetic screens probe modulations of complex biological processes rather than isolated targets (Schreiber et al (2003) and De Palma et al (2004)). A forward chemical genetic screen can be applied to identify compounds that are capable of inhibiting certain biological functions of cells, such as the proliferation of cancer cells. Cancer is defined by any malignant growth or tumor caused by abnormal and uncontrolled cell division. Therefore, compounds that inhibit abnormal and uncontrolled cell division might be useful as therapeutic compounds. By utilizing this approach potent and selective inhibitors can be found that inhibit vital functions of cells, such as cancer cell proliferation and are suitable in the treatment of cancer.

In chemical genetics screens, small molecule libraries are used to identify in high-throughput screens interesting compounds that interfere with a certain biological function of a cell. Typically, the libraries, used in these screens, consist of collections of diverse compounds with predicted drug-like properties.

The discovery of novel targets for e.g. angiogenesis inhibitors or cell proliferation inhibitors and validation of their biological relevancy based on chemical genetics provide in addition new insight for the biological role of certain targets as well valuable information for the development of new active compounds.

A forward chemical genetic screen has been applied to screen for compounds that are capable of inhibiting proliferation of cancer cells. This approach has led to a novel series of compounds useful for the treatment and/or prevention of proliferative diseases.

SUMMARY OF THE INVENTION

It is an object of the present invention to provide novel compounds of Formula (I)

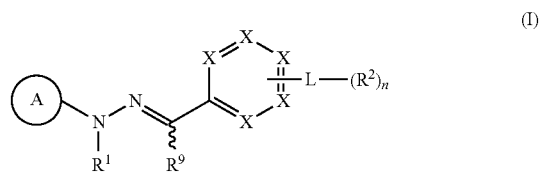

wherein A, X, L, $R^1$, $R^2$, $R^9$ and n are defined as described in the detailed description below, which are useful in the treatment of proliferative diseases.

The invention further provides a pharmaceutical composition comprising a compound of Formula (I), together with a pharmaceutically acceptable excipient or carrier.

Another aspect of the invention relates to the use of compounds of Formula (I) for the preparation of a medicament for the treatment of a proliferative disease.

The invention relates in another aspect to a method of treating a mammal suffering from or susceptible to a proliferative disease comprising administering to the mammal an effective amount of a compound of Formula (I).

Still another aspect of the invention relates to a method of inhibiting cancer cell proliferation, comprising contacting a cancer cell with a compound according to Formula (I) in an amount effective to inhibit the proliferation of the cancer cell.

Another aspect of the invention relates to a method of inhibiting angiogenesis, comprising contacting an endothelial cell with a compound according to Formula (I) in an amount effective to inhibit angiogenesis of said endothelial cell.

The invention further relates to methods to synthesize compounds of Formula (I).

DESCRIPTION OF THE INVENTION

The following paragraphs provide definitions of various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenanthrenyl and the like. The aryl ring may be also fused to a heterocycloalkyl group. Such fused aryls include dihydrobenzimidazole-2-one, benzo[1,3]dioxole and the like.

"$C_1$-$C_6$-alkyl aryl" refers to $C_1$-$C_6$-alkyl groups having an aryl substituent, such as, for example, benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4- triazinyl, 1,2,3-triazinyl, 1,3,4-thiadiazolyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, phthalazinyl, quinoxalinyl, cinnolinyl, napthyridinyl, pyridazinyl, pyrido[3,4-b]pyridyl, pyrido[3,2-b]pyridyl, pyrido[4,3-b]pyridyl, pyrido[2,3-d]pyrimidinyl, pyrido[4,3-d]pyrimidinyl, pyrido[3,4-d]pyrimidinyl, pyrido[3,2-d]pyrimidinyl, pyrimido[5,4d]pyrimidine, pyrimido[4,5d]pyrimidine, 7H-pyrrolo[2,3d]pyrimidinyl, 5H-pyrrolo[3,4d] pyrimidinyl, 5H-pyrrolo[2,3d]pyrimidinyl, 7H-purinyl, 1H[1,2,3]triazolo[4,5d]pyrimidinyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl and the like.

"$C_1$-$C_6$-alkyl heteroaryl" refers to $C_1$-$C_6$-alkyl groups having a heteroaryl substituent, such as, for example, 2-furylmethyl, 2-thienylmethyl, 2-(1H-indol-3-yl)ethyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_3$-$C_8$-heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, 1,4-dioxane and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"$C_2$-$C_6$-alkenyl" refers to alkenyl groups preferably having from 2 to 6 carbon atoms and having one or more sites of alkenyl unsaturation. Preferred alkenyl groups include ethenyl (—CH=$CH_2$), n-2-propenyl (allyl, —$CH_2$CH=$CH_2$) and the like.

"$C_2$-$C_6$-alkynyl" refers to alkynyl groups preferably having from 2 to 6 carbon atoms and having one or more sites of alkynyl unsaturation. Preferred alkynyl groups include ethynyl (—C≡CH), propynyl (—$CH_2$C≡CH), and the like.

"Carboxy" refers to the group —C(O)OR, where R includes hydrogen or "$C_1$-$C_6$-alkyl".

"Acyl" refers to the group —C(O)R where R includes "$C_1$-$C_6$-alkyl", "aryl", "heteroaryl", "$C_3$-$C_8$-cycloalkyl", "$C_3$-$C_8$-heterocycloalkyl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "hetero-aryl", "$C_1$-$C_6$-alkyl aryl" or "$C_1$-$C_6$-alkyl heteroaryl".

"Aryl acyl" refers to aryl groups having an acyl substituent, including 2-acetylphenyl and the like.

"Heteroaryl acyl" refers to heteroaryl groups having an acyl substituent, including 2-acetylpyridyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynyl heteroaryl", "$C_1$-$C_6$-alkyl cycloalkyl", "$C_1$-$C_6$-alkyl heterocycloalkyl". Preferred alkoxy groups include by way of example, methoxy, ethoxy, phenoxy and the like.

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl hetero-aryl".

"Acylamino" or "acylamine" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo substituents.

"Halo-$C_1$-$C_6$ alkyl" refers to a $C_1$-$C_6$-alkyl group having one or more halogen substituents. Preferred halo-$C_1$-$C_6$ alkyl groups include by way of example, trifluoromethyl, difluoromethyl and the like.

"Halo-$C_1$-$C_6$ alkoxy" refers to a $C_1$-$C_6$-alkoxy group having one or more halogen substituents. Preferred halo-$C_1$-$C_6$ alkoxy groups include by way of example, trifluoromethoxy, difluoromethoxy and the like.

"Hydroxy-$C_1$-$C_6$-alkyl" refers to a $C_1$-$C_6$-alkyl group having one or more hydroxyl substituents. Preferred hydroxy-$C_1$-$C_6$ alkyl groups include by way of example, hydroxymethyl, hydroxyethyl and the like.

"Thiourea" refers to the group —NRC(S)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfonyloxy" refers to a group —$OSO_2$—R wherein R is selected from H, "$C_1$-$C_6$-alkyl", "$C_1$-$C_6$-alkyl" substituted with halogens, e.g., an —$OSO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl","$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens, e.g., an —$SO_2$—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfinyl" refers to a group "—S(O)—R" wherein R is selected from H, "$C_1$-$C_6$-alkyl", "$C_1$-$C_6$-alkyl" substituted with halogens, e.g., an —SO—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Sulfanyl" refers to groups —S—R where R includes H, "$C_1$-$C_6$-alkyl", "$C_1$-$C_6$-alkyl" optionally substituted with halogens, e.g. a —S—$CF_3$ group, "$C_2$-$C_6$-alkenyl", "$C_2$-$C_6$-alkynyl", "$C_3$-$C_8$-cycloalkyl", "heterocycloalkyl", "aryl", "heteroaryl","$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$- alkynyl aryl", "C$_2$-C$_6$-alkynylheteroaryl", "C$_1$-C$_6$-alkyl cycloalkyl", "C$_1$-C$_6$-alkyl heterocycloalkyl". Preferred sulfanyl groups include methylsulfanyl, ethylsulfanyl, and the like.

"Sulfonylamino" refers to a group —NRSO$_2$—R' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"Aminosulfonyl" refers to a group —SO$_2$—NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"Amino" or "amine" refers to the group —NRR' where each R, R' is independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl", and where R and R', together with the nitrogen atom to which they are attached, can optionally form a 3-8-membered hetero-cycloalkyl ring.

"Substituted or unsubstituted": Unless otherwise constrained by the definition of the individual substituent, the above set out groups, like "alkyl", "alkenyl", "alkynyl", "alkoxy", "aryl" and "heteroaryl" etc. groups can optionally be substituted with from 1 to 5 substituents selected from the group consisting of "C$_1$-C$_6$-alkyl", "C$_1$-C$_6$-alkyl aryl", "C$_1$-C$_6$-alkyl heteroaryl", "C$_2$-C$_6$-alkenyl", "C$_2$-C$_6$-alkynyl", primary, secondary or tertiary amino groups or quaternary ammonium moieties, "acyl", "acyloxy", "acylamino", "aminocarbonyl", "alkoxycarbonyl", "aryl", "aryloxy", "heteroaryl", "heteroaryloxy", carboxyl, cyano, halogen, hydroxy, nitro, sulfanyl, sulphoxy, sulphonyl, sulfonamide, alkoxy, thioalkoxy, trihalomethyl and the like. Within the framework of this invention, said "substitution" is meant to also comprise situations where neighboring substituents undergo ring closure, in particular when vicinal functional substituents are involved, thus forming e.g. lactams, lactons, cyclic anhydrides, but also acetals, thioacetals, aminals formed by ring closure for instance in an effort to obtain a protective group.

"Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, 2-N-morpholinoethanol, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, meglumine (N-methylglucamine), benethamine (N-benzylphenethylamine), diethylamine, piperazine, thromethamine (2-amino-2-hydroxymethyl-1,3-propanediol), procaine as well as amines of formula —NR,R',R" wherein R, R', R" is independently hydrogen, alkyl or benzyl.

"Pharmaceutically acceptable salts or complexes" refers to salts or complexes of the below-identified compounds of Formula I that retain the desired biological activity. Examples of such salts include, but are not restricted to, acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the Formula —NR,R',R"$^+$ Z$^-$, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that, upon administration to the recipient, is capable of providing directly or indirectly, the activity disclosed herein.

In a first aspect the present invention provides compounds according to Formula (I) that are useful in the treatment and/or prevention of proliferative diseases.

In one embodiment, the invention provides compounds of Formula (I)

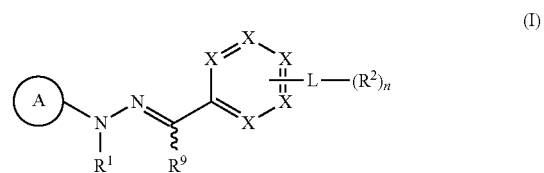

(I)

as well as its geometrical isomers, optically active forms as enantiomers, diastereomers, its tautomers, its racemate forms, as well as pharmaceutically acceptable salts or prodrug thereof, wherein:

A is selected from the group consisting of:

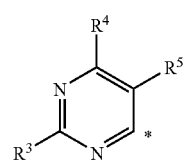

A1

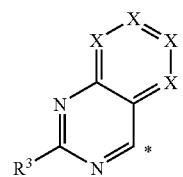

A2

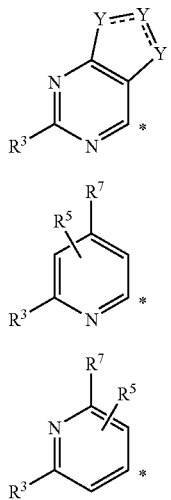

wherein * is the point of connection to the hydrazone backbone. A dotted line indicates a potential double bond.

Each X is independently selected from the group consisting of $CR^6$, N, and $NR^6$;

Each Y is independently selected from the group consisting of $CR^6$, N, $NR^6$, S and O;

L is either a bond or $NR^6$;

$R^1$, $R^6$ and $R^9$ are independently selected from either hydrogen or $C_1$-$C_6$-alkyl;

Each $R^2$ is independently selected from the group consisting of hydrogen, halogen, cyano, thioamide, acyl, $C_1$-$C_6$-alkyl, $C_2$-$C_6$-alkenyl, $C_2$-$C_6$-alkynyl, sulfonylamine, halo-$C_1$-$C_6$-alkyl, $C_1$-$C_6$-alkoxy, hydroxylamine, hydroxyl, $C_3$-$C_8$-cycloalkyl, $C_3$-$C_8$-heterocycloalkyl, aryl and heteroaryl;

n is an integer selected from 1, 2, 3, 4 or 5;

$R^3$ and $R^7$ are independently selected from the group consisting of hydrogen, halogen, cyano, thiourea, acylamine, carboxy, $C_1$-$C_6$-alkyl, $C_2$-$C_6$-alkenyl, $C_2$-$C_6$-alkynyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxylamine, hydroxyl, aryl and heteroaryl, wherein each of said $C_1$-$C_6$-alkyl, $C_2$-$C_6$-alkenyl, $C_2$-$C_6$-alkynyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxylamine, hydroxyl, aryl and heteroaryl is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, acylamine, hydroxy-$C_1$-$C_6$-alkyl, aryl and heteroaryl;

$R^5$ is selected from the group consisting of hydrogen, halogen, cyano, thiourea, amino, acylamine, carboxy, $C_1$-$C_6$-alkyl, $C_2$-$C_6$-alkenyl, $C_2$-$C_6$-alkynyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxylamine, hydroxyl, aryl and heteroaryl, wherein each of said $C_1$-$C_6$-alkyl, $C_2$-$C_6$-alkenyl, $C_2$-$C_6$-alkynyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxylamine, hydroxyl, aryl and heteroaryl is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, acylamine, hydroxy-$C_1$-$C_6$-alkyl, aryl and heteroaryl; $R^4$ is selected from the group consisting of $C_3$-$C_8$-cycloalkyl, $C_3$-$C_8$-heterocycloalkyl, aryl and heteroaryl bonded through a ring carbon, wherein each of said $C_3$-$C_8$-cycloalkyl, $C_3$-$C_8$-heterocycloalkyl, aryl and heteroaryl bonded through a ring carbon is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, aminocarbonyl, acylamine, hydroxy-$C_1$-$C_6$-alkyl, aryl and heteroaryl;

In a preferred embodiment the variants have the following meanings:

Each X is either $CR^6$ or N. In one embodiment at least one X is N. In a preferred embodiment X is $CR^6$.

L is either a bond or $NR^6$. In one embodiment L is a bond. In another embodiment L is NH.

$R^1$ is either hydrogen or $C_1$-$C_6$-alkyl; preferably $R^1$ is selected from the group consisting of hydrogen, methyl, or ethyl.

Each $R^2$ is independently selected from the group consisting of hydrogen, halogen, cyano, thioamide, acyl, thiourea, acylamine, carboxy, $C_1$-$C_6$-alkyl, sulfonylamine, halo-$C_1$-$C_6$-alkyl, $C_1$-$C_6$-alkoxy, hydroxylamine and hydroxyl; preferably $R^2$ is independently selected from the group consisting of hydrogen, methyl, ethyl, acyl, thioamide, chloro, methoxy, bromo and fluoro.

n is an integer selected from 1, 2, or 3. Preferably n is either 1 or 2.

$R^3$ is selected from the group consisting of hydrogen, halogen, cyano, thiourea, acylamine, carboxy, $C_1$-$C_6$-alkyl, halo-$C_1$-$C_6$-alkyl and $C_1$-$C_6$-alkoxy. Preferably $R^3$ is selected from the group consisting of hydrogen, methyl, ethyl, methoxy and ethoxy.

In another embodiment $R^3$ is selected from the group of halogen, cyano, thiourea, acylamine, carboxy, $C_1$-$C_6$-alkyl, halo-$C_1$-$C_6$-alkyl and $C_1$-$C_6$-alkoxy.

$R^4$ is either aryl or an heteroaryl bonded through a ring carbon, wherein said aryl or heteroaryl bonded through a ring carbon is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, acylamine, hydroxy-$C_1$-$C_6$-alkyl, aryl and heteroaryl.

Preferred heteroaryls are selected from the group consisting of:

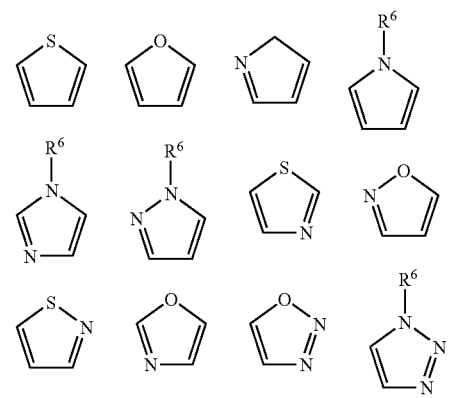

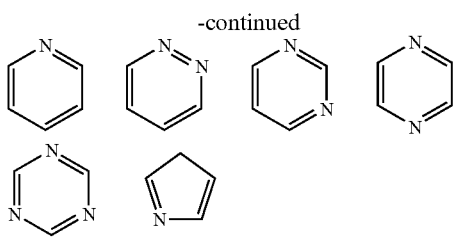

Each of said heteroaryl is connected to the pyrimidyl backbone through a ring carbon and is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, acylamine, hydroxy-$C_1$-$C_6$-alkyl, aryl and heteroaryl.

Preferably $R^4$ is selected from the group consisting of phenyl, pyridyl and isoxazolyl, wherein each of said phenyl, pyridyl and isoxazolyl is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, acylamine, hydroxy-$C_1$-$C_6$-alkyl, aryl and heteroaryl.

$R^5$ is selected from the group consisting of hydrogen, halogen, cyano, $C_1$-$C_6$-alkyl, sulfonylamine, thiourea, amino, acylamine, carboxy, halo-$C_1$-$C_6$-alkyl, $C_1$-$C_6$-alkoxy, halo-$C_1$-$C_6$-alkoxy, hydroxylamine and hydroxyl.

$R^6$ is either hydrogen or $C_1$-$C_6$-alkyl; preferably $R^6$ is either hydrogen.

$R^7$ is selected from the group consisting of aryl, heteroaryl, $C_3$-$C_8$-cycloalkyl and $C_3$-$C_8$-heterocycloalkyl, wherein each of said aryl, heteroaryl, $C_3$-$C_8$-cycloalkyl and $C_3$-$C_8$-heterocycloalkyl is optionally substituted with one or more substituents selected from the group consisting of halogen, amine, cyano, $C_1$-$C_6$-alkyl, $C_2$-$C_6$-alkenyl, $C_3$-$C_8$-cycloalkyl, $C_3$-$C_8$-heterocycloalkyl, sulfonylamine, halo-$C_1$-$C_6$-alkyl, $C_1$-$C_6$-alkoxy, halo-$C_1$-$C_6$-alkoxy, hydroxyl, acylamine, hydroxy-$C_1$-$C_6$-alkyl, aryl and heteroaryl.

$R^9$ is either hydrogen or $C_1$-$C_6$-alkyl; preferably $R^9$ is selected from the group consisting of hydrogen, methyl and ethyl.

In another embodiment the compounds of the invention are further defined by a specific sub-group of Formula (I), defined by Formula (II):

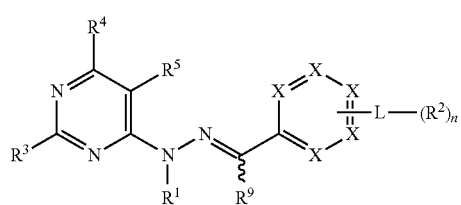

wherein X, L $R^1$, $R^2$, $R^3$, $R^4$, $R^5$, $R^9$ and n are as defined above.

In one embodiment the X is $CR^6$ and L is $NR^6$, wherein $R^6$ is independently either hydrogen or $C_1$-$C_6$-alkyl; preferably $R^6$ is selected from the group consisting of hydrogen, methyl, or ethyl.

In another embodiment the compounds of the invention are further defined by a specific sub-group of Formula (I), defined Formula (III):

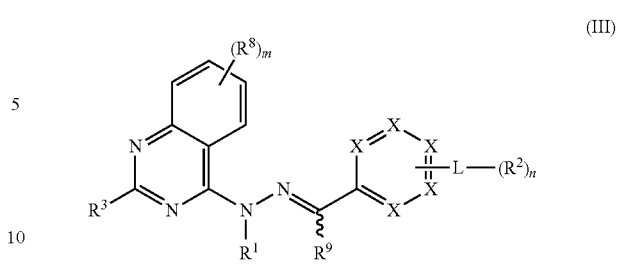

wherein X, L $R^1$, $R^2$, $R^3$, $R^9$ and n are as defined above and each $R^8$ is independently selected from the group consisting of hydrogen, halogen, cyano, $C_1$-$C_6$-alkyl, sulfonylamine, thiourea, acylamine, carboxy, halo-$C_1$-$C_6$-alkyl, $C_1$-$C_6$-alkoxy, halo-$C_1$-$C_6$-alkoxy, hydroxylamine and hydroxyl; and m is an integer selected from 1, 2, 3, or 4. Preferably m is either 1 or 2

In one embodiment the X is $CR^6$ and L is a bond, wherein $R^6$ is either hydrogen or $C_1$-$C_6$-alkyl; preferably $R^6$ is selected from the group consisting of hydrogen, methyl, or ethyl.

In one embodiment $R^3$ is selected from the group consisting of halogen, cyano, thiourea, acylamine, carboxy, $C_1$-$C_6$-alkyl, halo-$C_1$-$C_6$-alkyl and $C_1$-$C_6$-alkoxy. Preferably $R^3$ is selected from the group consisting of methyl, ethyl, methoxy and ethoxy.

Compounds of Formulae (I), (II) and (III) exist as isomers as shown generally for compounds of Formula (I). Pure isomers as well as racemic mixtures of the compounds are within the scope of the invention.

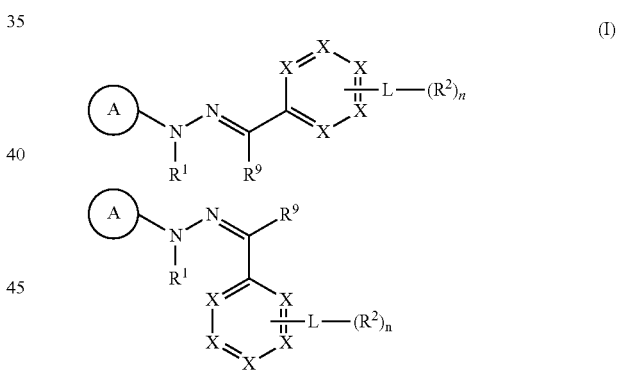

Tautomers of the above-shown structures are also within the scope of the invention.

Preferred pharmaceutically acceptable salts or complexes of compounds of Formula (I), and compounds of sub-groups of Formulae (II) and (III) are also within the scope of the invention.

Compounds of the present invention that are particularly suitable for the treatment and/or prevention of proliferative diseases, include in particular those selected from the group consisting of:

| Compound No. | Compound name |
|---|---|
| 1 | N-Methyl-N'-(1-m-tolyl-ethylidene)-N-(2-trifluoromethylquinazolin-4-yl-hydrazine |

-continued

| Compound No. | Compound name |
|---|---|
| 2 | N-Methyl-N'-(1-p-tolyl-ethylidene)-N-(2-trifluoromethylquinazolin-4-yl-hydrazine |
| 3 | N-(1-p-Tolyl-ethylidene)-N'-(2-trifluoromethyl-quinazolin-4-yl)-hydrazine |
| 4 | N-[1-(4-methoxy-phenyl)-ethylidene]-N'-(2-methyl-quinazolin-4-yl)-hydrazine |
| 5 | N-(2-Methyl-quinazolin-4-yl)-N-(1-p-tolyl-ethylidene)-hydrazine |
| 6 | N-(2-methyl-quinazolin-4-yl)-N'-(1-m-tolyl-ethylidene)-hydrazine |
| 7 | N-Methyl-N-(2-methyl-quinazolin-4-yl)-N-(1-p-tolyl-ethylidene)-hydrazine |
| 8 | Dimethyl-(4-{1-[(2-methyl-6-phenyl-pyrimidin-4-yl)-hydrazono]ethyl}-phenyl) amine |
| 9 | 4-(1-{[6-(2-Methoxy-phenyl)-2-methyl-pyrimidin-4-yl]-hydrazono}-ethyl)-phenyl]-dimethylamine |
| 10 | (4-(1-{[6-(3,5-dimethyl-isoxazol-4-yl)-2-methyl-pyrimidin-4-yl]-hydrazono}-ethyl)-phenyl]-dimethylamine |
| 11 | Dimethyl-[4-(1-{[2-methyl-6-(2-trifluoromethoxy-phenyl)-pyrimidin-4-yl]-hydrazono}-ethyl)-phenyl]-amine |
| 12 | [4-(1-{[6-(2-Isopropoxy-phenyl)-2-methyl-pyrimidin-4-yl]-hydrazono}-ethyl)-phenyl]-dimethylamine |
| 13 | [4-(1-{[6-(2-Fluoro-phenyl)-2-methyl-pyrimidin-4-yl]-hydrazono}-ethyl)-phenyl]-dimethylamine |
| 14 | [4-(1-{[6-(2-amino-phenyl)-2-methyl-pyrimidin-4-yl]-hydrazono}-ethyl)-phenyl]-dimethylamine |
| 15 | (4-{1-[(2-Methoxy-6-phenyl-pyrimidin-4-yl)-hydrazono]-ethyl}-phenyl)-dimethylamine |
| 16 | [4-(1 {[2-Ethyl-6-(2-methoxy-phenyl)-pyrimidin-4-yl]-hydrazono}-ethyl)-phenyl]-dimethylamine |
| 17 | [4-(1-{[6-(2-Methoxy-phenyl)-pyrimidin-4-yl]-hydrazono}-ethyl)-phenyl] dimethyl amine |
| 18 | Methyl-(4-{1-[(2-methyl-6-phenyl-pyrimidin-4-yl)-hydrazono]-ethyl}-phenyl)-amine |
| 19 | 4-{1-[(2-Methyl-6-phenyl-pyrimidin-4-yl)-hydrazono]-ethyl}-phenyl)-thiourea |
| 20 | N-(4-{1-[(2-Methyl-6-phenyl-pyrimidin-4-yl)-hydrazono]-ethyl}-phenyl)-acetamide |
| 21 | 2-Methyl-4-{N'-[1-(4-methylamino-phenyl)-ethylidene]-hydrazino}-6-phenyl-pyrimidin-5-ylamine |
| 22 | N-(2-Methyl-6-phenyl-pyrimidin-4-yl)-N'-[1-p-tolyl-propylidene]-hydrazine |
| 23 | N-[1-(4-Chloro-phenyl)ethylidene]-N'-(2-methyl-6-phenyl-pyrimidin-4-yl)-hydrazine |
| 24 | N-[1-(4-Methoxy-phenyl)-ethylidene]-N'-(2-methyl-6-phenyl-pyrimidin-4-yl)-hydrazine |
| 25 | N-[6-(2-Methoxy-phenyl)-pyrimidin-4-yl]-N'-[1-p-tolyl-ethylidene]-hydrazine |
| 26 | N-[2-Ethyl-6-(2-methoxy-phenyl)-pyrimidin-4-yl]-N'-[1-p-tolyl-ethylidene]-hydrazine |
| 27 | N-[6-(2-Fluoro-phenyl)-2-methyl-pyrimidin-4-yl]-N'-[1-p-tolyl-ethylidene]-hydrazine |
| 28 | N-[6-(3-Methoxy-phenyl)-2-methyl pyrimidin-4-yl]-N'-[1-p-tolyl-ethylidene]-hydrazine |
| 29 | N-[6-(2-Methoxy-phenyl)-2-methyl pyrimidin-4-yl]-N'-[1-p-tolyl-ethylidene]-hydrazine |
| 30 | N-[6-(4-Methoxy-phenyl)-2-methyl pyrimidin-4-yl]-N'-[1-p-tolyl-ethylidene]-hydrazine |
| 31 | 2-(2-Methyl-6-{N'-[1-p-tolyl-ethylidene]-hydrazino}-pyrimidin-4-yl)-benzonitrile |
| 32 | N-[6-(2-methyl-phenyl)-2-methyl-pyrimidin-4-yl]-N'-[1-p-tolyl-ethylidene]-hydrazine |
| 33 | N-[2-Methyl-6-(2-morpholin-4-yl-phenyl)-pyrimidin-4-yl]-N'-[1-p-tolyl-ethylidene]-hydrazine |
| 34 | N-[2-(2-Methyl-6-{N'-[1-p-tolyl-ethylidene]-hydrazino}-pyrimidin-4-yl)-phenyl]-acetamide |
| 35 | [2-(2-Methyl-6-{N'-[1-p-tolyl-ethylidene]-hydrazino}-pyrimidin-4-yl)-phenyl]-methanol |
| 36 | N-[6-(3,5-Dimethyl-isoxazol-4-yl)-2-methyl-pyrimidin-4-yl]-N'-[1-p-tolyl-ethylidene]-hydrazine |
| 37 | N-(2-Methyl-6-pyridin-3-yl-pyrimidin-4-yl)-N'-[1-p-tolyl-ethylidene]-hydrazine |
| 38 | 2-(2-Methyl-6-{N'-[1-p-tolyl-ethylidene]-hydrazino}-pyrimidin-4-yl)-phenylamine |
| 39 | N-Methyl-N-(2-methyl-6-phenyl-pyrimidin-4-yl)-N'-[1-p-tolyl-ethylidene]-hydrazine |
| 40 | N-[6-(2,6-Dimethoxy-phenyl)-2-methyl-pyrimidin-4-yl]-N'-[1-p-tolyl-ethylidene]-hydrazine |

In a second aspect, the invention provides a pharmaceutical composition comprising at least one compound according to Formulae (I), (II) or (III), together with a pharmaceutically acceptable excipient or carrier.

In a third aspect, the invention provides the use of compounds according to Formulae (I), (II) or (III) for the preparation of a medicament for the treatment of a proliferative disease. In one embodiment the proliferative disease is cancer.

In a fourth aspect, the invention provides the use of compounds according to Formulae (I), (II) or (III) for the treatment and/or prevention of a proliferative disease. In one embodiment the proliferative disease is cancer.

In a fifth aspect, the invention provides a method of treating a mammal suffering from or susceptible to a proliferative disease comprising administering to the mammal an effective amount of a compound of Formula (I).

In one embodiment the proliferative disease is cancer.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

The compounds according to Formulae (I), (II) or (III) of the present invention are typically administered in form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions.

In such compositions, the substituted methylene amide derivative according to the invention is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as pepper-mint, methyl salicylate, or orange flavoring.

Injectable compositions are typically based upon injectable sterile saline or phosphate buffered saline or other injectable carriers known in the art. As above mentioned, substituted methylene amide derivatives of Formula (I) in such compositions is typically a minor component, frequently ranging between 0.05 to 10% by weight with the remainder being the injectable carrier and the like.

The above-described components for orally administered or injectable compositions are merely representative. Further materials as well as processing techniques and the like are set out in Part 5 of *Remington's Pharmaceutical Sciences*, 20th Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

The compounds of this invention can also be administered in combination with anti-cancer agents. Examples of such anti-cancer agent may include alkylating agents, antimitotic agents, topo I inhibitors, topo II inhibitors, RNA/DNA antimetabolites, EGFR inhibitors, angiogenesis inhibitors, tubulin inhibitors (e.g., vinblastine, paclitaxel and analogues thereof), proteosome inhibitors. Exemplary compounds may include melphalan, chlorambucil, cyclophosphamide, ifosfamide, vincristine, mitoguazone, epirubicin, aclarubicin, bleomycin, mitoxantrone, elliptinium, fludarabine, ocreotide, retinoic acid, tamoxifen, Gleevec (imatinib mesylate) and alanosine.

In a sixth aspect the invention relates to a method of inhibiting cancer cell proliferation, comprising contacting a cancer cell with a compound according to Formulae (I), (II) or (III) in an amount effective to inhibit the proliferation of the cancer cell.

In a seventh aspect the invention relates to a method of inhibiting angiogenesis, comprising contacting an endothelial cell with a compound according to Formulae (I), (II) or (III) in an amount effective to inhibit the formation of endothelial tubes (angiogenesis) of said cell.

In one embodiment the compound of Formulae (I), (II) or (III) is selected from the consisting group of:

| Compound No. | Compound name |
|---|---|
| 1 | N-Methyl-N'-(1-m-tolyl-ethylidene)-N-(2-trifluoromethylquinazolin-4-yl-hydrazine |
| 2 | N-Methyl-N'-(1-p-tolyl-ethylidene)-N-(2-trifluoromethylquinazolin-4-yl-hydrazine |
| 3 | N-(1-p-Tolyl-ethylidene)-N'-(2-trifluoromethyl-quinazolin-4-yl)-hydrazine |
| 4 | N-[1-(4-methoxy-phenyl)-ethylidene]-N'-(2-methyl-quinazolin-4-yl)-hydrazine |
| 5 | N-(2-Methyl-quinazolin-4-yl)-N-(1-p-tolyl-ethylidene)-hydrazine |
| 6 | N-(2-methyl-quinazolin-4-yl)-N'-(1-m-tolyl-ethylidene)-hydrazine |
| 7 | N-Methyl-N-(2-methyl-quinazolin-4-yl)-N-(1-p-tolyl-ethylidene)-hydrazine |
| 8 | Dimethyl-(4-{1-[(2-methyl-6-phenyl-pyrimidin-4-yl)-hydrazono]ethyl}-phenyl) amine |
| 9 | 4-(1-{[6-(2-Methoxy-phenyl)-2-methyl-pyrimidin-4-yl]-hydrazono}-ethyl)-phenyl)-dimethylamine |
| 10 | (4-(1-{[6-(3,5-dimethyl-isoxazol-4-yl)-2-methyl-pyrimidin-4-yl]-hydrazono}-ethyl)-phenyl]-dimethylamine |
| 11 | Dimethyl-[4-(1-{[2-methyl-6-(2-trifluoromethoxy-phenyl)-pyrimidin-4-yl]-hydrazono}-ethyl)-phenyl]-amine |
| 12 | [4-(1-{[6-(2-Isopropoxy-phenyl)-2-methyl-pyrimidin-4-yl]-hydrazono}-ethyl)-phenyl]-dimethylamine |
| 13 | [4-(1-{[6-(2-Fluoro-phenyl)-2-methyl-pyrimidin-4-yl]-hydrazono}-ethyl)-phenyl]-dimethylamine |
| 14 | [4-(1-{[6-(2-amino-phenyl)-2-methyl-pyrimidin-4-yl]-hydrazono}-ethyl)-phenyl]-dimethylamine |
| 15 | (4-{1-[(2-Methoxy-6-phenyl-pyrimidin-4-yl)-hydrazono]-ethyl}-phenyl)-dimethylamine |
| 16 | [4-(1 {[2-Ethyl-6-(2-methoxy-phenyl)-pyrimidin-4-yl]-hydrazono}-ethyl)-phenyl]-dimethylamine |
| 17 | [4-(1-{[6-(2-Methoxy-phenyl)-pyrimidin-4-yl]-hydrazono}-ethyl-phenyl] dimethyl amine |
| 18 | Methyl-(4-{1-[(2-methyl-6-phenyl-pyrimidin-4-yl)-hydrazono]-ethyl}-phenyl)-amine |
| 19 | 4-{1-[(2-Methyl-6-phenyl-pyrimidin-4-yl)-hydrazono]-ethyl}-phenyl)-thiourea |
| 20 | N-(4-{1-[(2-Methyl-6-phenyl-pyrimidin-4-yl)-hydrazono]-ethyl}-phenyl)-acetamide |
| 21 | 2-Methyl-4-{N'-[1-(4-methylamino-phenyl)-ethylidene]-hydrazino}-6-phenyl-pyrimidin-5-ylamine |
| 22 | N-(2-Methyl-6-phenyl-pyrimidin-4-yl)-N'-[1-p-tolyl-propylidene]-hydrazine |
| 23 | N-[1-(4-Chloro-phenyl)ethylidene]-N'-(2-methyl-6-phenyl-pyrimidin-4-yl)-hydrazine |
| 24 | N-[1-(4-Methoxy-phenyl)-ethylidene]-N'-(2-methyl-6-phenyl-pyrimidin-4-yl)-hydrazine |
| 25 | N-[6-(2-Methoxy-phenyl)-pyrimidin-4-yl]-N'-[1-p-tolyl-ethylidene]-hydrazine |
| 26 | N-[2-Ethyl-6-(2-methoxy-phenyl)-pyrimidin-4-yl]-N'-[1-p-tolyl-ethylidene]-hydrazine |
| 27 | N-[6-(2-Fluoro-phenyl)-2-methyl-pyrimidin-4-yl]-N'-[1-p-tolyl-ethylidene]-hydrazine |
| 28 | N-[6-(3-Methoxy-phenyl)-2-methyl pyrimidin-4-yl]-N'-[1-p-tolyl-ethylidene]-hydrazine |
| 29 | N-[6-(2-Methoxy-phenyl)-2-methyl pyrimidin-4-yl]-N'-[1-p-tolyl-ethylidene]-hydrazine |
| 30 | N-[6-(4-Methoxy-phenyl)-2-methyl pyrimidin-4-yl]-N'-[1-p-tolyl-ethylidene]-hydrazine |
| 31 | 2-(2-Methyl-6-{N'-[1-p-tolyl-ethylidene-hydrazino}-pyrimidin-4-yl)-benzonitrile |
| 32 | N-[6-(2-methyl-phenyl)-2-methyl-pyrimidin-4-yl]-N'-[1-p-tolyl-ethylidene]-hydrazine |
| 33 | N-[2-Methyl-6-(2-morpholin-4-yl-phenyl)-pyrimidin-4-yl]-N'-[1-p-tolyl-ethylidene]-hydrazine |
| 34 | N-[2-(2-Methyl-6-{N'-[1-p-tolyl-ethylidene]-hydrazino}-pyrimidin-4-yl)-phenyl]-acetamide |
| 35 | [2-(2-Methyl-6-{N'-[1-p-tolyl-ethylidene]-hydrazino}-pyrimidin-4-yl)-phenyl]-methanol |
| 36 | N-[6-(3,5-Dimethyl-isoxazol-4-yl)-2-methyl-pyrimidin-4-yl]-N'-[1-p-tolyl-ethylidene]-hydrazine |
| 37 | N-(2-Methyl-6-pyridin-3-yl-pyrimidin-4-yl)-N'-[1-p-tolyl-ethylidene]-hydrazine |
| 38 | 2-(2-Methyl-6-{N'-[1-p-tolyl-ethylidene]-hydrazino}-pyrimidin-4-yl)-phenylamine |
| 39 | N-Methyl-N-(2-methyl-6-phenyl-pyrimidin-4-yl)-N'-[1-p-tolyl-ethylidene]-hydrazine |

-continued

| Compound No. | Compound name |
|---|---|
| 40 | N-[6-(2,6-Dimethoxy-phenyl)-2-methyl-pyrimidin-4-yl]-N'-[1-p-tolyl-ethylidene]-hydrazine |
| 41 | N-(2-Methyl-6-phenyl-pyrimidin-4-yl)-N'-(1-p-tolyl-ethylidene)-hydrazine |
| 42 | 4-{1-[(2-Methyl-6-phenyl-pyrimidin-4-yl)-hydrazono]-ethyl}-phenylamine |
| 43 | N-[1-(4-Ethyl-phenyl)-ethylidene]-N'-(2-methyl-6-phenyl-pyrimidin-4-yl)-hydrazine |
| 44 | N-[1-(4-Bromo-phenyl)-ethylidene]-N'-(2-methyl-6-phenyl-pyrimidin-4-yl)-hydrazine |
| 45 | N-[1-(4-Iodo-phenyl)-ethylidene]-N'-(2-methyl-6-phenyl-pyrimidin-4-yl)-hydrazine |
| 46 | 3-{1-[(2-Methyl-6-phenyl-pyrimidin-4-yl)-hydrazono]-ethyl}-phenylamine |
| 47 | N-[1-(3,4-Dichloro-phenyl)-ethylidene]-N'-(2-methyl-6-phenyl-pyrimidin-4-yl)-hydrazine |
| 48 | 4-{1-[(2-Methyl-6-phenyl-pyrimidin-4-yl)-hydrazono]-ethyl}-phenol |

In an eighth aspect, the invention provides a method of synthesis of a compound according to Formula (I).

The compounds exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approach for obtaining compounds of Formula (I) is depicted in Scheme 1. The hydrazine 1 is condensed with the carbonyl derivative 2 to yield compounds of Formula (I). $R^1$, $R^2$, $R^9$, X, L and n are as above defined.

Preparation of the Compounds of Formula (I)

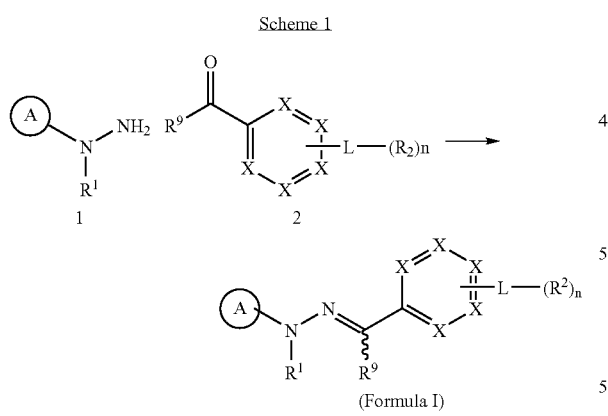

Scheme 1

A further objective of the present invention is a process for preparing hydrazone derivatives according to sub-formulae of Formula (I), namely Formulae (II) and (III).

Preparation of the Compounds of Formula (II) Hydrazone

According to one synthetic approach, the pyrimidin-4-yl derivatives, whereby the substituents $R^1$, $R^2$, $R^3$, $R^4$, $R^9$, L and n are as above defined, are prepared from the pyrimidine 3 using standard synthetic techniques hereinafter described in the examples and shown in schemes 2a and 2b.

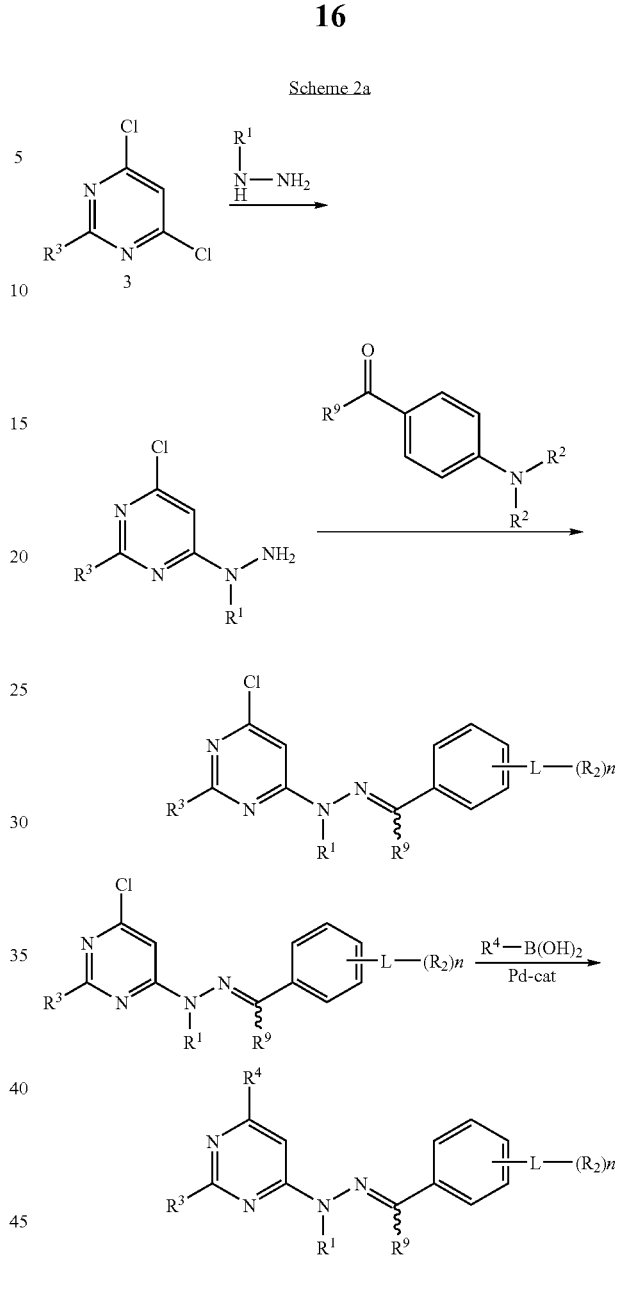

Scheme 2a

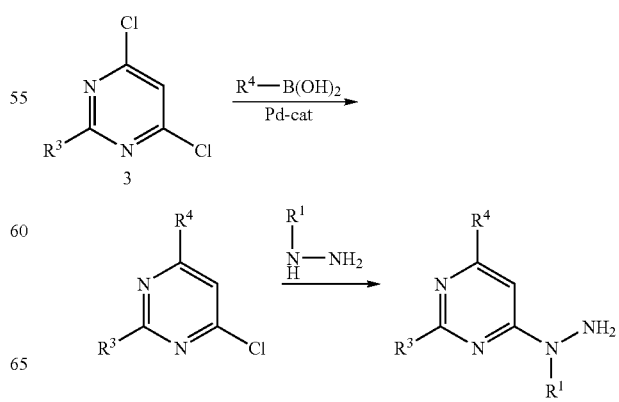

Scheme 2b

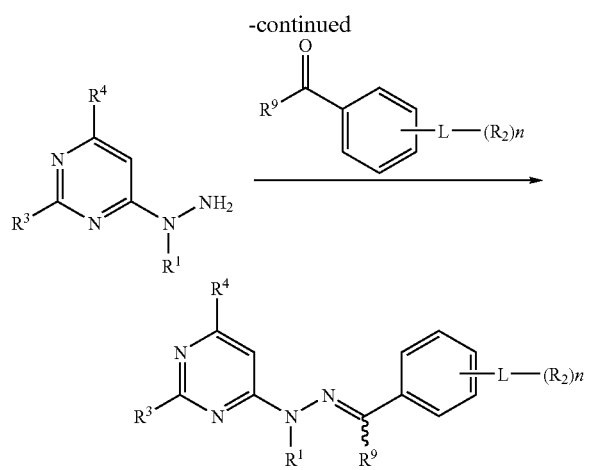

a) Preparation of the Compounds of Formula (III)

The quinazolin-4-yl hydrazone, whereby the substituents L, $R^1$, $R^2$, $R^3$, $R^8$, $R^9$, L, m and n are as above defined, are prepared from the quinazolinone 4 using standard synthetic techniques hereinafter described in the examples and shown in scheme 3.

Scheme 3

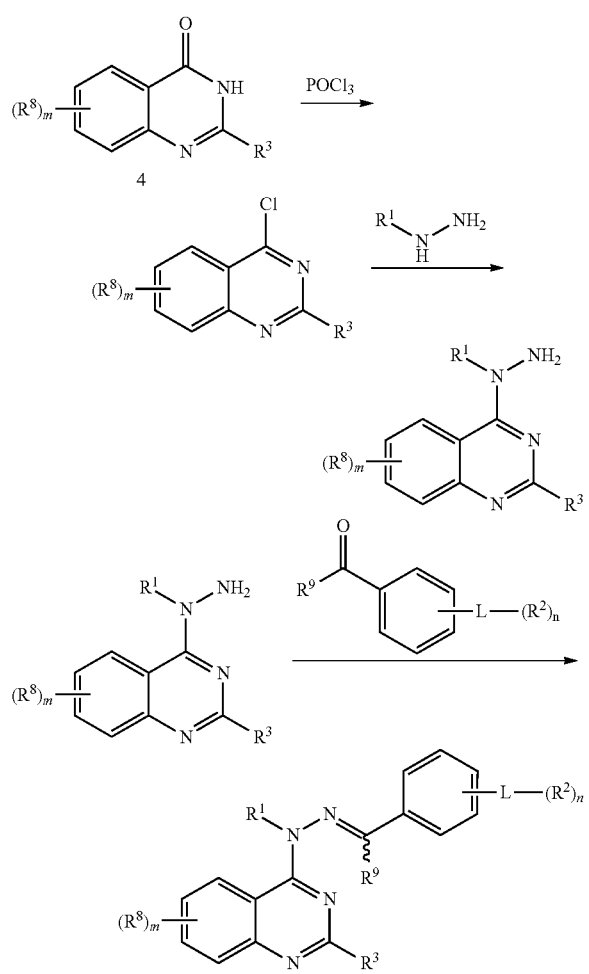

If the above set out general synthetic methods are not applicable for obtaining compounds according to Formula I and/or necessary intermediates for the synthesis of compounds of Formula (I), suitable methods of preparation known by a person skilled on the art should be used. In general, the synthesis pathways for any individual compound of formula (I), (II) or (III) will depend on the specific substituents of each molecule and upon the ready availability of intermediates necessary; again such factors being appreciated by those of ordinary skill in the art. For all protection, deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley-Interscience, 1991.

Compounds of this invention can be isolated in association with solvent molecules by crystallization from evaporation of an appropriate solvent. The pharmaceutically acceptable acid addition salts of the compounds of Formula (I), which contain a basic center, may be prepared in the conventional manner. For example, a solution of the free base may be treated with a suitable acid, either neat or in a suitable solution and the resulting salt isolated either by filtration or by evaporation under vacuum of the reaction solvent. Pharmaceutically acceptable base addition salts of the compounds of Formula (I), which contain an acidic center, may be obtained in analogous manner by treating a solution of compound of the Formula (I) with suitable base. Both types of salt may be formed or interconverted using ion-exchange resin techniques.

The following abbreviations refer respectively to the definitions below:

min (minute), hr (hour), g (gram), MHz (Megahertz), ml (milliliter), mmol (millimole), mM (millimolar), RT (room temperature), ATP (Adenoside Triphosphate), BSA (Bovine Serum Albumin), DCM (dichloromethane), DIPEA (di-isopropyl ethylamine), DMSO (Dimethyl Sulfoxide), DMF (N,N-Dimethylformamide), $CsCO_3$ (Cesium carbonate), cHex (Cyclohexanes), $Et_3N$ (Triethylamine), EtOAc (Ethyl acetate), EtOH (Ethanol), $K_2CO_3$ (potassium carbonate), NaI (Sodium Iodine), KCN, (Potassium cyanide), NaH (Sodium hydride), $NaHCO_3$ (Sodium bicarbonate), $NH_4Cl$ (Ammonium chloride), TEA (Triethyl amine), TFA (Trifluoroacetic acid), THF (Tetrahydrofuran), HCl (hydrogen chloride), tBuOK (Potassium tert-butoxide), MeOH (Methanol), $MgSO_4$ (Magnesium sulfate), PetEther (Petroleum ether), rt (room temperature). HPLC (High Performance Liquid Chromatography), FC (Flash Chromatography on silica gel), MS (Mass Spectrometry), NMR (Nuclear Magnetic Resonance), PBS (Phosphate Buffered Saline), SPA (Scintillation Proximity Assay), TLC (Thin Layer Chromatography), UV (Ultraviolet).

Experimental Part

The HPLC, NMR and MS data provided in the examples described below are obtained as followed: Agilent 1100 HPLC: column Waters Symmetry C18 50×4.6 mm, Conditions: A. H2O with 0.1% Formic acid and B. MeOH with 0.1% Formic acid. A from 15% to 95% (8 min), LC/MS: Agilent 1100 HPLC/LCQ Duo (ESI), $^1$H-NMR: Jeol ECP-400 MHz, Bruker 300 MHz and Bruker 400 MHz. TLC Analysis is performed on Merck Precoated 60 F254 plates. Purifications by flash chromatography are performed on $SiO_2$ support.

EXAMPLES

The invention will be illustrated by means of the following examples that are not to be construed as limiting the scope of the invention.

Example 1

N-Methyl-N'-(1-m-tolyl-ethylidene)-N-(2-trifluoromethylquinazolin-4-yl-hydrazine Step-1: 2-(Trifluoromethyl)quinazolin-4(3H)-one

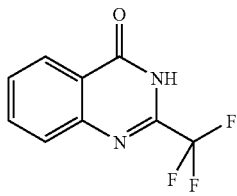

To a freshly prepared solution of sodium ethoxide in ethanol (8.5 g of sodium metal was dissolved in 300 ml of ethanol) was added anthranilamide (25 g, 0.183 mol) in portions and the mixture was stirred under nitrogen at 60° C. for 1 h. To this was added ethyl trifluoro acetate (26 g, 0.183 mol) and the mixture was maintained at this temperature for 20 h with stirring. The reaction mixture was cooled and the solvent was removed under vacuum. The residue was acidified with 1.5N HCl and the solid precipitated was collected by filtration to afford 12 g (31%) of the titled compound as an off-white solid.

MP: 243-246° C., LCMS: Mass found (M−1, 212.8), $^1$H NMR (CD$_3$OD, 300 MHz) δ 7.69-7.74 (1H, m), 7.86-7.89 (1H, m), 7.93-7.98 (1H, m), 8.30-8.33 (1H, m).

Step-2: 4-Chloro-2-(trifluoromethyl)quinazoline

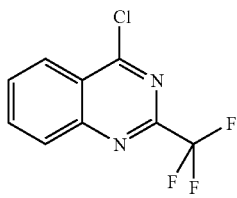

To a mixture of 2-(trifluoromethyl)quinazolin-4(3H)-one (12 g) and phosphorous oxychloride (100 ml) was added DMF (0.5 ml) and the mixture was refluxed under nitrogen for 16 h. The excess phosphorous oxychloride was distilled off and the residue was diluted with ethyl acetate (200 ml). The ethyl acetate layer was washed with 10% solution of sodium bicarbonate, water and brine. The solvent was dried and evaporated. The residue was purified by chromatography (silica gel: 60-120 mesh) eluting with pet ether/ethyl acetate (9/1) to afford 8 g (61%) of the titled compound as a pale yellow solid.

MP: 62-63.5° C., LCMS: Mass found (M+1, 233), $^1$H NMR (CDCl$_3$, 300 MHz) δ 7.88-7.93 (1H, m), 8.09-8.14 (1H, m), 8.23-8.26 (1H, m), 8.37-8.40 (1H, m).

Step-3: 4-(1-Methylhydrazino)-2-(trifluoromethyl)quinazoline

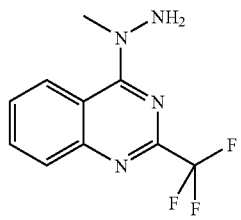

To a solution of 4-chloro-2-(trifluoromethyl)quinazoline (8 g, 0.0344 mol) in dry dichloromethane (100 ml) under nitrogen was added methyl hydrazine (1.74 g, 0.037 mol) and the mixture was stirred at room temperature for 5 h. The reaction mixture was washed with water (2×100 ml), brine and dried. The solvent was removed under vacuum to afford 8 g (96%) of the titled compound as a yellow solid.

MP: 130-132° C., LCMS: Mass found (M+1, 243), $^1$H NMR (DMSO-d6, 300 MHz) δ 3.49 (3H, s), 5.53 (2H, bs), 7.50-7.55 (1H, m), 7.75-7.84 (2H, m), 9.67-9.70 (1H, d).

Step 4: N-Methyl-N'-(1-m-tolyl-ethylidene)-N-(2-trifluoromethylquinazolin-4-yl-hydrazine

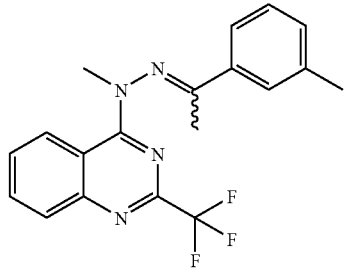

To a solution of 4-(1-methylhydrazino)-2-(trifluoromethyl)quinazoline (250 mg, 1.03 mmol) and 3'-methylacetophenone (0.14 mL, 1.03 mmol) in ethanol were heated in a sealed tube in a 110 C oil bath. After approximately 48 hours the reaction mixture was concentrated in vacuo. An initial purification by Si gel chromatography utilizing hexanes:ethyl acetate (19:2) was performed. A subsequent crystallization from ethyl acetate and hexanes yielded 128.9 mg (35%) of the title compound as a pale yellow solid. HPLC Purity: 98%.

LCMS: Mass Found (M+1, 360), $^1$H NMR (DMSO-d6, 400 MHz) δ 8.28 (d, J=8.79 Hz, 1H), 7.81-7.92 (m, 4H), 7.53 (t, J=7.5 Hz, 1H), 7.41-7.46 (m, 2H), 3.54 (s, 3H), 2.56 (s, 3H), 2.40 (s, 3H).

Example 2

N-Methyl-N'-(1-p-tolyl-ethylidene)-N-(2-trifluoromethylquinazolin-4-yl-hydrazine

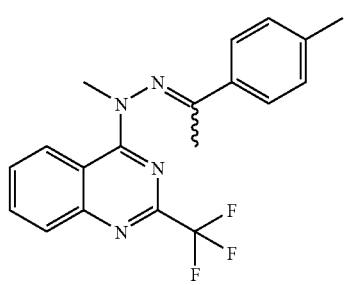

The title compound was prepared from 4-(1-methylhydrazino)-2-(trifluoromethyl)quinazoline (250 mg, 1.03 mmol) and 4'-methylacetophenone (0.30 mL, 2.06 mmol) by a procedure similar to Example 1, Step 4 yielding 32.4 mg (9%) of a crystalline yellow solid. HPLC Purity: 98%.

LCMS: Mass Found (M+1, 360), ¹H NMR: (DMSO-d6, 400 MHz) δ 8.29 (d, J=8.42 Hz, 1H), 7.83-7.93 (m, 4H), 7.50 (m, 1H), 7.36 (d, J=8.06 Hz, 2H), 3.54 (s, 3H), 2.54 (s, 3H), 2.40 (s, 3H).

Example 3

N-(1-p-Tolyl-ethylidene)-N'-(2-trifluoromethyl-quinazolin-4-yl)-hydrazine

Step 1: (2-Trifluoromethyl-quinazolin-4-yl)-hydrazine

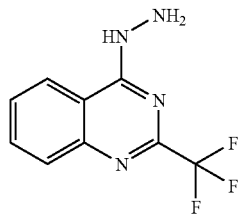

To a solution of 4-chloro-2-(trifluoromethyl)quinazoline (2.0 g, 8.6 mmol) and hydrazine (0.27 mL, 8.6 mmol) in 20 mL of tetrahydrofuran was added 1.8 g (13 mmol) of potassium carbonate. The resultant suspension was stirred at ambient temperature for 2 hours. The reaction mixture was partitioned between ethyl acetate and water. The aqueous layer was extracted with ethyl acetate and the combined organics were dried over magnesium sulfate. After filtration, the organics were concentrated in vacuo to yield a yellow solid that was recrystallized in ethyl acetate:hexanes. 1.1 g (56%) of yellow needle-like crystals were isolated.

LCMS: Mass Found (M+1, 229), ¹H NMR: (DMSO-d6, 400 MHz) δ 10.2 (bs, 1H), 8.28 (d, J=8.06 Hz, 1H), 7.81-7.89 (m, 2H), 4.96 (bs, 2H).

Step 2: N-(1-p-Tolyl-ethylidene)-N'-(2-trifluoromethyl-quinazolin-4-yl)-hydrazine

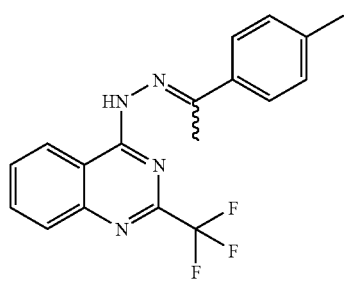

The title compound was prepared from (2-trifluoromethyl-quinazolin-4-yl)-hydrazine (250 mg, 1.1 mmol) and 4'-methylacetophenone (0.22 mL, 1.6 mmol) by a procedure similar to Example 1, step 4 yielding 225 mg (60%) of a yellow solid. HPLC Purity: 95%.

LCMS: Mass Found (M+1, 345), ¹H NMR: (CD₃OD, 400 MHz) δ 7.94 (m, 3H), 7.81 (d, J=8.24 Hz, 2H), 7.67 (m, 1H), 7.28 (d, J=8.24 Hz, 2H), 2.48 (s, 3H), 2.39 (s, 3H).

Example 4

N-[1-(4-methoxy-phenyl)-ethylidene]-N'-(2-methyl-quinazolin-4-yl)-hydrazine

Step-1: 2-Methylquinazolin-4(3H)-one

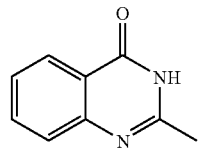

A mixture of 2-amino benzamide (20 g, 0.147 mol) and acetamide (43 g, 0.735 mol) was heated to 180° C. for 20 h. The dark brown reaction mixture was cooled and suspended in ethanol (200 ml). After stirring for 2 h, it was filtered and dried under suction to afford 11 g (47%) of the titled compound as a brown solid.

LCMS: Mass found (M+1, 161.5), ¹H NMR (DMSO-d6: 300 MHz) δ 2.33 (3H, s), 7.41-7.46 (1H, m), 7.54-7.57 (1H, m), 7.73-7.78 (1H, m), 8.04-8.07 (1H, m), 12.02 (1H, bs)

Step-2: 4-Chloro-2-methylquinazoline

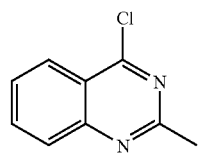

To a mixture of 2-methylquinazolin-4(3H)-one (9.2 g, 0.0574 mol) and phosphorous oxychloride (5.8 g, 0.037 mol) in dry toluene (250 ml) was added N,N-dimethyl aniline (13.9 g, 0.14 mol) and the mixture was refluxed for 3 h. The reaction mixture was cooled and washed with water, brine and dried. The solvent was removed under vacuum and the residue was purified by chromatography (silica gel, 60-120 mesh) eluting with pet ether/ethyl acetate (9/1) to afford 4 g (39%) of the titled compound as a solid.

LCMS: Mass found (M+1, 178.9), ¹H NMR (CDCl₃: 300 MHz) δ 2.86 (3H, s), 7.63-7.68 (1H, m), 7.89-7.98 (2H, m), 8.21-8.24 (1H, m).

Step-3: 4-Hydrazino-2-methylquinazoline dihydrochloride

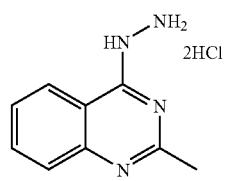

To a solution of 4-chloro-2-methylquinazoline (2 g, 0.111 mol) in dry THF (50 ml) was added potassium carbonate (2.3 g, 0.016 mol) followed by anhydrous hydrazine (0.43 g, 0.013 mol). The reaction mixture was stirred at room temperature for 2 h and filtered. The filtrate was evaporated under reduced pressure and the residue was treated with HCl in dioxane (2M, 50 ml). The solid precipitated was filtered and dried under vacuum to afford 2 g (74%) of the titled compound as a yellow solid.

MP: 297.3-305.8° C., LCMS: Mass found (M+1, 174.9), $^1$H NMR (CD$_3$OD: 300 MHz) δ 3.35 (3H, s), 7.84-7.90 (2H, m), 8.12-8.15 (1H, m), 8.37-8.40 (1H, m).

Step 4: N-[1-(4-methoxy-phenyl)-ethylidene]-N'-(2-methyl-quinazolin-4-yl)-hydrazine

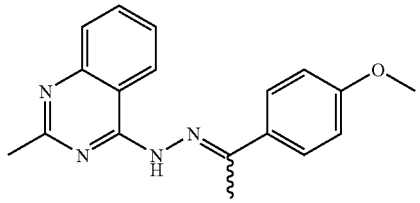

To a solution of 4-hydrazino-2-methylquinazoline dihydrochloride (100 mg, 0.40 mmol) and triethylamine (0.14 mL, 0.81 mmol) in ethanol (3 mL) was added 61 mg (0.4 mmol) of 4-methoxyacetophenone. The resultant solution was refluxed overnight and the resultant reaction mixture was absorbed directly on Si gel. Purification by automated Si gel chromatography (gradient 100% hexanes to 100% ethyl acetate) on the Flashmaster II was performed yielding 50 mg (36%) of the titled compound as a bright yellow solid. HPLC Purity: 91%.

LCMS: Mass Found (M+1, 307), $^1$H NMR: (CD$_3$OD, 400 MHz) δ 8.24 (d, J=8.04 Hz, 1H), 7.97 (d, J=9.06 Hz, 2H), 7.59 (t, J=7.34 Hz, 1H), 7.37 (m, 2H), 6.74 (d, J=9.06 Hz, 2H), 4.85 (s, 3H), 2.51 (s, 3H), 2.40 (s, 3H).

Example 5

N-(2-Methyl-quinazolin-4-yl)-N-(1-p-tolyl-ethylidene)-hydrazine

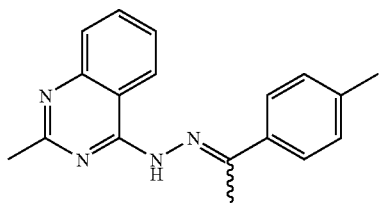

The title compound was prepared from 4-hydrazino-2-methylquinazoline dihydrochloride (150 mg, 0.61 mmol), triethylamine (0.17 mL, 1.22 mmol) and 4-methylacetophenone (0.11 mL, 1.36 mmol) in ethanol (1.2 mL) by a procedure similar to Example 4, step 4 yielding 82 mg (47%) of a yellow solid. HPLC Purity: 98%.

LCMS: Mass Found (M+1, 291), $^1$H NMR: (CD$_3$OD, 400 MHz) δ 8.25 (d, J=7.69 Hz, 1H), 7.88 (d, J=8.43 Hz, 2H), 7.59 (t, J=7.52 Hz, 1H), 7.37 (m, 2H), 7.23 (d, J=8.43 Hz, 2H), 2.54 (s, 3H), 2.40 (s, 3H), 2.38 (s, 3H).

Example 6

N-(2-methyl-quinazolin-4-yl)-N'-(1-m-tolyl-ethylidene)-hydrazine

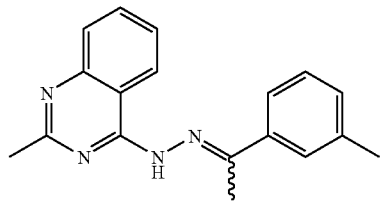

The title compound was prepared from 4-hydrazino-2-methylquinazoline dihydrochloride (250 mg, 1.01 mmol), triethylamine (0.35 mL, 2.02 mmol) and 3-methylacetophenone (0.35 mL, 2.63 mmol) in ethanol (5 mL) by a procedure similar to Example 4, step 4 yielding 11 mg (4%) of a yellow solid. HPLC Purity: 95%.

MS: Mass Found (M+1, 291), $^1$H NMR: (CDCl$_3$, 400 MHz) δ 8.3 (m, 1H), 7.55-7.65 (m, 4H), 7.25-7.40 (m, 3H), 2.6 (s, 3H), 2.4 (2S, 6H).

Example 7

N-Methyl-N-(2-methyl-quinazolin-4-yl)-N-(1-p-tolyl-ethylidene)-hydrazine

Step 1: N-Methyl-N-(2-methyl-quinazolin-4-yl)-hydrazine

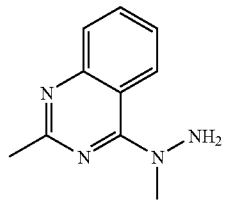

The title compound was prepared from 4-chloro-2-methylquinazoline (1.0 g, 5.6 mmol), N-methylhydrazine (0.89 mL, 16.8 mmol) and potassium carbonate (1.3 g, 22.4 mmol) in dry THF (20 mL) by a procedure similar to example 1, step 3 yielding 380 mg (36%) of a beige solid.

$^1$H NMR: (CD$_3$OD, 400 MHz) δ 9.44 (d, J=9.52 Hz, 1H), 7.59-7.64 (m, 2H), 7.31 (t, J=6.48 Hz, 1H), 3.54 (s, 3H), 2.50 (s, 3H).

Step 2: N-Methyl-N-(2-methyl-quinazolin-4-yl)-N-(1-p-tolyl-ethylidene)-hydrazine

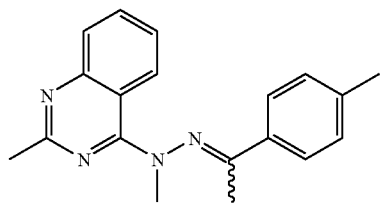

The title compound was prepared from N-methyl-N-(2-methyl-quinazoliny-4-yl)-hydrazine (380 mg, 2.0 mmol) and 4-methylacetophenone (0.30 mL, 2.2 mmol) in ethanol (20 mL) by a procedure similar to example 1, step 4 yielding 15 mg (2.4%) of a pale yellow solid. HPLC Purity: 98%.

$^1$H NMR: (CD$_3$OD, 400 MHz) δ 8.16 (d, J=8.42 Hz, 1H), 7.90 (d, J=8.24 Hz, 2H), 7.68 (d, J=3.30 Hz, 2H), 7.31 (d, J=8.24 Hz, 2H), 7.26 (m, 1H), 3.52 (s, 3H), 2.62 (s, 3H), 2.62 (s, 3H), 2.52 (s, 3H), 2.41 (s, 3H).

Example 8

Dimethyl-(4-{1-[(2-methyl-6-phenyl-pyrimidin-4-yl)-hydrazono]ethyl}-phenyl)amine Step-1: 2-Methyl-6-phenylpyrimidin-4(3H)-one

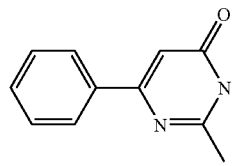

To a freshly prepared solution of sodium ethoxide (18 g of sodium metal was dissolved in 1 L of ethanol), was added ethyl benzoyl acetate (75 g, 0.39 mol) and the mixture was stirred at room temperature for 30 min. To this was added acetamidine hydrochloride (37 g, 0.39 mol) in portions and the mixture was refluxed for 24 h under nitrogen. The reaction mixture was cooled and excess ethanol was removed under vacuum. The residue was acidified to pH=4 with 1.5N HCl and the precipitate was filtered and dried under suction to afford 15 g (21%) of the titled compound as a white solid.

MP: 238.5-240° C., MS: Mass found (M+1, 186.9), $^1$H NMR (CD$_3$OD, 300 MHz) δ 2.51 (3H, s), 6.73 (1H, s), 7.52 (3H, m), 8.01-8.02 (2H, m).

Step-2: 4-Chloro-2-methyl-6-phenylpyrimidine

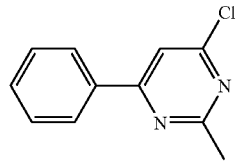

A mixture of 2-methyl-6-phenylpyrimidin-4(3H)-one (15 g) and POCl$_3$ (150 ml) was refluxed under nitrogen for 20 h. The excess POCl$_3$ was distilled off and the residue was diluted with ethyl acetate (500 ml) and washed with 10% solution of sodium bicarbonate (100 ml), water, brine and dried. The solvent was removed under reduced pressure and the residue was purified by chromatography (silica, 60-120 mesh) eluting with pet ether/ethyl acetate (9/1) to afford 11 g (67%) of the titled as a pale yellow solid.

MP: 57-59° C., MS: Mass found (M+1, 204.9), $^1$H NMR (DMSO-d6, 400 MHz) δ 2.50 (3H, s), 7.52-7.58 (3H, m), 8.08 (1H, s), 8.20-8.22 (2H, m).

Step-3: 4-Hydrazino-2-methyl-6-phenylpyrimidine trihydrochloride

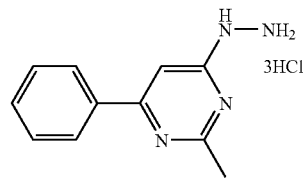

To a solution of 4-chloro-2-methyl-6-phenylpyrimidine (11 g, 0.0537 mol) in dioxane (100 ml) was added anhydrous hydrazine (2 g, 0.0625 mol) followed by potassium carbonate (11 g, 0.080 mol) and the reaction mixture was stirred at room temperature for 6 h. The reaction mixture was filtered and the filtrate was evaporated under reduced pressure. The residue was treated with 2M HCl in dioxane (100 ml) and the solid precipitated was filtered and washed with methanol (100 ml) and dried under suction to afford 10 g (60%) of the titled compound as a solid.

MP: 225-229.6° C., MS: Mass found (M+1, 200.9), $^1$H NMR (DMSO-d6, 300 MHz) δ 2.72 (3H, s), 7.25 (1H, s), 7.61-7.67 (3H, m), 7.95-7.97 (2H, m), 8.79 (4H, vbs)

Step 4: Dimethyl-(4-{1-[(2-methyl-6-phenyl-pyrimidin-4-yl)-hydrazono]ethyl}-phenyl)amine

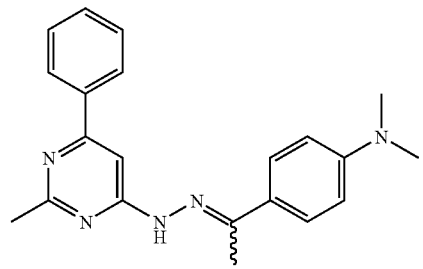

To a solution of 4-hydrazino-2-methyl-6-phenylpyrimidine trihydrochloride (300 mg, 0.97 mmol) and diisopropylethylamine (0.17 mL, 0.97 mmol) in ethanol (10 mL) was added 4-dimethylaminoacetophenone (158 mg, 0.97 mmol). The resultant reaction mixture was heated at reflux overnight. The reaction mixture was diluted with dIH$_2$O and the pH was adjusted to 1-2 and washed with ethyl acetate. The pH of the aqueous layer was adjusted to 9-10 and was extracted with ethyl acetate. The combined extracts were concentrated in vacuo and the residue crystallized from ethyl acetate:hexanes. 60 mg (18%) of the title compound was isolated as a yellow solid. HPLC Purity: 98%.

LCMS: Mass Found (M+1, 346), $^1$H NMR: (CD$_3$OD, 400 MHz) δ 7.95 (m, 2H), 7.75 (d, J=8.97 Hz, 2H), 7.49-7.51 (m, 3H), 7.40 (brs, 1H), 6.77 (d, J=8.97 Hz, 2H), 2.99 (s, 6H), 2.55 (s, 3H), 2.30 (s, 3H).

Example 9

4-(1-{[6-(2-Methoxy-phenyl)-2-methyl-pyrimidin-4-yl]-hydrazono}-ethyl)-phenyl]-dimethylamine Step-1: 4-Chloro-6-hydrazino-2-methylpyrimidine

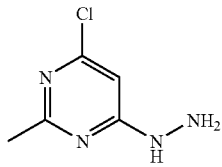

To a solution of 4,6-dichloro-2-methylpyrimidine (10 g, 0.061 mol) in dry THF (500 ml) was added anhydrous hydrazine (1.96 g, 0.061 mol) followed by potassium carbonate (12.7 g, 0.092 mol). The reaction mixture was stirred at room temperature for 13 h and filtered. The filtrate was evaporated under reduced pressure to afford 9.3 g (45%) of the titled compound as a solid.

MP: 164-172° C., MS: Mass found (M+1, 158.9), $^1$H NMR (CDCl$_3$, 300 MHz): δ 2.49 (3H, s), 3.05 (2H, bs), 6.59 (1H, bs), 6.67 (1H, s).

Step-2: (1)-1-[4-(Dimethylamino)phenyl]ethanone (6-chloro-2-methylpyrimidin-4-yl)hydrazone

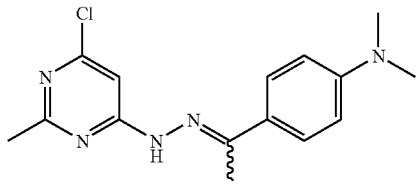

To a solution of 4-chloro-6-hydrazino-2-methylpyrimidine (5 g, 0.0315 mol) in dry toluene (100 ml) was added 4-N,N-dimethylamino acetophenone (5.1 g, 0.0315 mol) and the mixture was azeotropically refluxed under nitrogen for 40 h. The reaction mixture was cooled and the solvent was removed under reduced pressure. The residue was crystallized from pet ether/ethyl acetate to afford 3.3 g (38%) of the titled compound as a solid.

MP: 163-164.6° C., MS: Mass found (m/z, M+ 304), $^1$H NMR (CDCl$_3$, 400 MHz): δ 2.30 (3H, s), 2.52 (3H, s), 3.07 (6H, s), 6.72-6.75 (2H, d), 7.14 (1H, s), 7.70-7.72 (1H, d), 8.34 (1H, bs).

Step 3: [4-(1-{[6-(2-Methoxy-phenyl)-2-methyl-pyrimidin-4-yl]-hydrazono}-ethyl)-phenyl]-dimethylamine

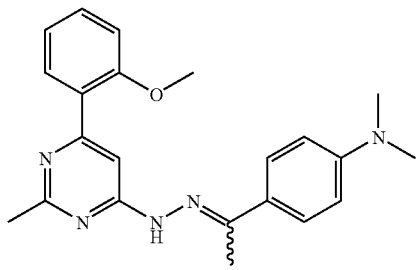

To a solution of (1)-1-[4-(dimethylamino)phenyl]ethanone (6-chloro-2-methylpyrimidin-4-yl)hydrazone (250 mg, 0.82 mmol) in anhydrous 1,4-dioxane (8 mL) in a sealed tube was added 2-methoxyphenylboronic acid (625 mg, 4.1 mmol), 1,3-bis(2,4,6-trimethylphenyl)imidazolium chloride (39 mg, 0.12 mmol), tris(dibenzylideneacetone)dipalladium (53 mg, 0.06 mmol) and cesium carbonate (1.61 g, 4.9 mmol). The reaction mixture was heated overnight in a 100° C. oil bath. After absorbing the reaction mixture directly on Si gel, chromatography was performed on the Flashmaster II (gradient 100% hexanes to 100% ethyl acetate) affording 260 mg (84%) of the title compound as a brown solid. HPLC Purity: 96%.

LCMS: Mass found (M+1, 376), $^1$H NMR: (CDCl$_3$, 400 MHz) δ 8.16 (brs, 1H), 7.84 (dd, J=1.48, 7.32 Hz, 1H), 7.70 (d, J=9.16 Hz, 2H), 7.64 (s, 1H), 7.38 (m, 1H), 7.07 (t, J=7.5 Hz, 1H), 7.00 (d, J=8.4 Hz, 1H), 6.68 (d, J=9.16 Hz, 2H), 3.89 (s, 3H), 2.98 (s, 6H), 2.62 (s, 3H), 2.21 (s, 3H).

Example 10

(4-(1-{[6-(3,5-dimethyl-isoxazol-4-yl)-2-methyl-pyrimidin-4-yl]-hydrazono}-ethyl)-phenyl]-dimethylamine

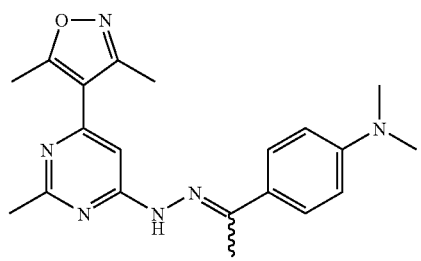

The title compound was prepared from (1)-1-[4-(dimethylamino)phenyl]ethanone (6-chloro-2-methylpyrimidin-4-yl) hydrazone (100 mg, 0.33 mmol), 3,5-dimethylisoxazole-4-boronic acid (139 mg, 0.99 mmol), 1,3-bis(2,4,6-trimethylphenyl)imidazolium chloride (16 mg, 0.05 mmol), tris(dibenzylideneacetone)dipalladium (21 mg, 0.02 mmol) and cesium carbonate (386 mg, 1.2 mmol) in 1,4-dioxane (4 mL) by a procedure similar to Example 9, Step 3 yielding 23 mg (19%) of a light grayish brown solid. HPLC Purity: 98%.

LCMS: Mass found (M+1, 356), $^1$H NMR: (CDCl$_3$, 400 MHz) δ 7.67 (d, J=8.98 Hz, 2H), 7.25 (s, 1H), 7.15 (s, 1H), 6.71 (d, J=8.98 Hz, 2H), 3.00 (s, 6H), 2.66 (s, 3H), 2.57 (s, 3H), 2.48 (s, 3H), 2.25 (s, 3H).

Example 11

Dimethyl-[4-(1-{[2-methyl-6-(2-trifluoromethoxy-phenyl)-pyrimidin-4-yl]-hydrazono}-ethyl)-phenyl]-amine

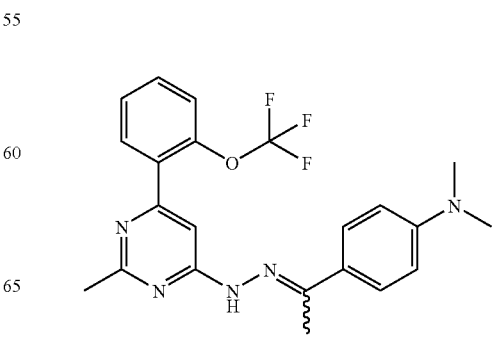

The title compound was prepared from (1)-1-[4-(dimethylamino)phenyl]ethanone (6-chloro-2-methylpyrimidin-4-yl) hydrazone (100 mg, 0.33 mmol), 2-trifluoromethoxyphenylboronic acid (203 mg, 0.99 mmol), 1,3-bis(2,4,6-trimethylphenyl)imidazolium chloride (16 mg, 0.05 mmol), tris(dibenzylideneacetone)dipalladium (21 mg, 0.02 mmol) and cesium carbonate (386 mg, 1.2 mmol) in 1,4-dioxane (4 mL) by a procedure similar to Example 9, Step 3 yielding 103 mg (73%) of a brown solid. HPLC Purity: 91%.

LCMS: Mass Found (M+1, 430), $^1$H NMR: (CDCl$_3$, 400 MHz) δ 7.90 (m, 1H), 7.69 (d, J=9.16 Hz, 2H), 7.51 (s, 1H), 7.34-7.48 (m, 2H), 6.71 (d, J=9.16 Hz, 2H), 3.00 (s, 6H), 2.62 (s, 3H), 2.34 (s, 3H).

Example 12

[4-(1-{[6-(2-Isopropoxy-phenyl)-2-methyl-pyrimidin-4-yl]-hydrazono}-ethyl)-phenyl]-dimethylamine

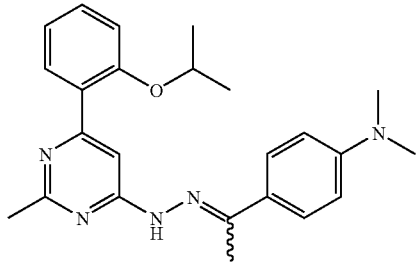

The title compound was prepared from (1)-1-[4-(dimethylamino)phenyl]ethanone (6-chloro-2-methylpyrimidin-4-yl) hydrazone (100 mg, 0.33 mmol), 2-isopropoxyphenylboronic acid (178 mg, 0.99 mmol), 1,3-bis(2,4,6-trimethylphenyl)imidazolium chloride (16 mg, 0.05 mmol), tris(dibenzylideneacetone)dipalladium (21 mg, 0.02 mmol) and cesium carbonate (386 mg, 1.2 mmol) in 1,4-dioxane (4 mL) by a procedure similar to Example 9, Step 3 yielding 73 mg (55%) of a brown solid. HPLC Purity: 95%.

LCMS: Mass Found (M+1, 404; M+Na, 426), $^1$H NMR: (CDCl$_3$, 400 MHz) δ 8.18 (brs, 1H), 7.98 (d, J=7.69 Hz, 1H), 7.86 (s, 1H), 7.72 (d, J=8.97 Hz, 2H), 7.34 (m, 1H), 7.05 (t, J=7.32 Hz, 1H), 7.01 (d, J=8.08 Hz, 1H), 6.67 (d, J=8.97 Hz, 2H), 4.60 (m, 1H), 2.97 (s, 6H), 2.62 (s, 3H), 2.21 (s, 3H), 1.37 (d, J=5.86 Hz, 6H).

Example 13

[4-(1-{[6-(2-Fluoro-phenyl)-2-methyl-pyrimidin-4-yl]-hydrazono}-ethyl)-phenyl]-dimethylamine

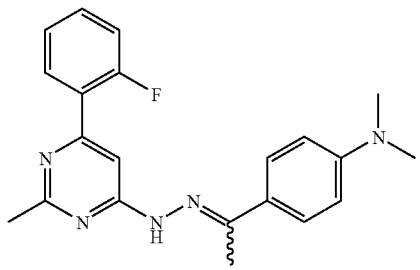

The title compound was prepared from (1)-1-[4-(dimethylamino)phenyl]ethanone (6-chloro-2-methylpyrimidin-4-yl) hydrazone (250 mg, 0.82 mmol), 2-fluorophenylboronic acid (576 mg, 4.1 mmol), 1,3-bis(2,4,6-trimethylphenyl)imidazolium chloride (39 mg, 0.12 mmol), tris(dibenzylideneacetone)dipalladium (53 mg, 0.06 mmol) and cesium carbonate (1.6 g, 4.9 mmol) in 1,4-dioxane (8 mL) by a procedure similar to Example 9, Step 3 yielding 225 mg (75%) of a dark brown solid. HPLC Purity: 98%.

LCMS: Mass Found (M+1, 364), $^1$H NMR: (CDCl$_3$, 400 MHz) δ 8.25 (brs, 1H), 8.04 (m, 1H), 7.70 (d, J=8.79 Hz, 2H), 7.59 (s, 1H), 7.39 (m, 1H), 7.26 (m, 1H), 7.16 (m, 1H), 6.69 (d, J=8.79 Hz, 2H), 2.98 (s, 6H), 2.62 (s, 3H), 2.18 (s, 3H).

Example 14

[4-(1-{[6-(2-amino-phenyl)-2-methyl-pyrimidin-4-yl]-hydrazono}-ethyl)-phenyl]-dimethylamine

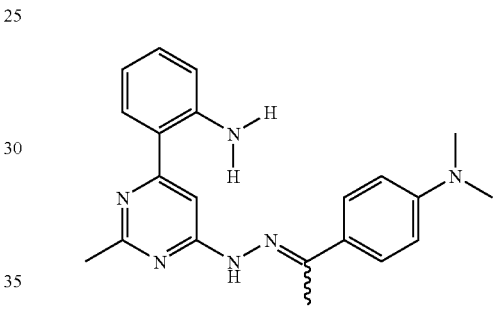

[2-(6-{N'-[1-(4-dimethylamino-phenyl)-ethylidene]-hydrazino}-2-methyl-pyrimidin-4-yl)-phenyl]-carbamic acid tert-butyl ester was prepared from (1)-1-[4-(dimethylamino)phenyl]ethanone (6-chloro-2-methylpyrimidin-4-yl)hydrazone (250 mg, 0.82 mmol), 2-tert-butoxycarbonylaminophenyl boronic acid (975 mg, 4.1 mmol), 1,3-bis(2,4,6-trimethylphenyl)imidazolium chloride (39 mg, 0.12 mmol), tris(dibenzylideneacetone)dipalladium (53 mg, 0.06 mmol) and cesium carbonate (1.6 g, 4.9 mmol) in 1,4-dioxane (8 mL) by a procedure similar to Example 9, Step 3 yielding 304 mg (80%).

[2-(6-{N'-[1-(4-dimethylamino-phenyl)-ethylidene]-hydrazino}-2-methyl-pyrimidin-4-yl)-phenyl]-carbamic acid tert-butyl ester was dissolved in 10 mL of 5% trifluoroacetic acid in dichloromethane. The resultant reaction mixture was stirred at room temperature for 2 hours before being concentrated in vacuo. The residue was dissolved in methanol and the pH was adjusted to 7 with potassium bicarbonate. After filtration the methanol was concentrated in vacuo and the residue was purified by Si gel chromatography (1:1 ethyl acetate:hexanes) yielding 140 mg (60%) of the title compound as a brown solid. HPLC Purity: 95%.

LCMS: Mass Found (M+1, 361), $^1$H NMR: (CD$_3$OD, 400 MHz) δ 7.66 (d, J=8.79 Hz, 2H), 7.50 (dd, J=1.46, 7.69 Hz, 1H), 7.26 (s, 1H), 7.15 (m, 1H), 6.66-6.80 (m, 4H), 2.96 (s, 6H), 2.49 (s, 3H), 2.21 (s, 3H).

Example 15

(4-{1-[(2-Methoxy-6-phenyl-pyrimidin-4-yl)-hydrazono]-ethyl}-phenyl)-dimethylamine Step 1: 2-Methoxy-pyrimidine-4,6-diol

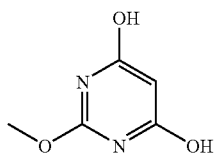

In a sealed tube O-methylisourea hydrochloride (3.0 g, 27 mmol) and dimethyl malonate (3.1 mL, 27 mmol) were dissolved in 30% w/v solution of sodium methoxide in methanol. The reaction mixture was refluxed for four hours before being allowed to cool to ambient temperature overnight. The resultant white precipitate was filtered and dried in vacuo yielding 4.2 g (quantitative yield) of the title compound.

$^1$H NMR: (DMSO-d6, 400 MHz) δ 10.21 (brs, 1H), 4.09 (s, 1H), 3.65 (s, 3H).

Step 2: 4,6-dichloro-2-methoxy-pyrimidine

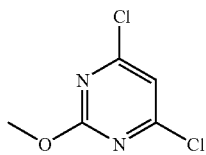

2-Methoxy-pyrimidine-4,6-diol was dissolved in phosphorous oxychloride and the resultant reaction mixture was refluxed for four hours. After quenching with basic ice-water, the resultant aqueous mixture was extracted with ethyl acetate and the combined extracts dried over magnesium sulfate. The organics were concentrated in vacuo yielding 1.1 g (44%, crude yield) of the title compound.

LCMS: Mass Found (M+1, 179)

Step 3: (6-Chloro-2-methoxy-pyrimidin-4-yl) hydrazine

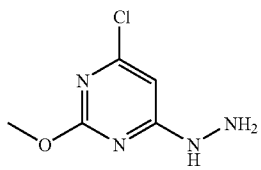

4,6-dichloro-2-methoxy-pyrimidine (1.1 g, 6.2 mmol) was dissolved in 100 mL of anhydrous tetrahydrofuran. To the resultant reaction solution hydrazine (0.19 mL, 6.2 mmol) and potassium carbonate (2.6 g, 18 mmol) were added and the reaction mixture was stirred for 3 days. The potassium carbonate was removed by filtration and the filtrate was concentrated in vacuo. Crystallization of the residue from ethyl acetate:hexanes yielded 414 mg (39%) of the title compound.

1H NMR: (DMSO-d6, 400 MHz) δ 8.80 (s, 1H), 6.49 (brs, 1H), 4.50 (brs, 2H), 3.77 (s, 3H).

Step 4: (4-{1-[(6-Chloro-2-methoxy-pyrimidin-4-yl)hydrazono]-ethyl}-phenyl)-dimethylamine

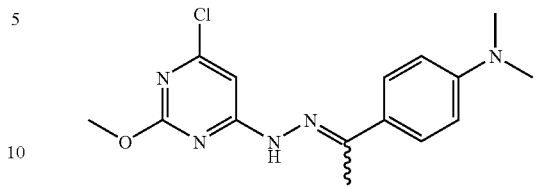

The title compound was prepared from (6-chloro-2-methoxy-pyrimidin-4-yl)hydrazine (414 mg, 2.4 mmol) and 4-dimethylaminoacetophenone (387 mg, 2.4 mmol) in ethanol (10 mL) by a procedure similar to Example 1, step 4 yielding 305 mg (40%).

LCMS: Mass Found (M+1, 320), $^1$H NMR: (CDCl$_3$, 400 MHz) δ 8.23 (brs, 1H), 7.70 (d, J=8.79 Hz, 2H), 6.96 (s, 1H), 6.76 (brs, 1H), 3.96 (s, 3H), 3.02 (s, 6H), 2.23 (s, 3H).

Step 5: (4-{1-[(2-Methoxy-6-phenyl-pyrimidin-4-yl)-hydrazono]-ethyl}-phenyl)-dimethylamine

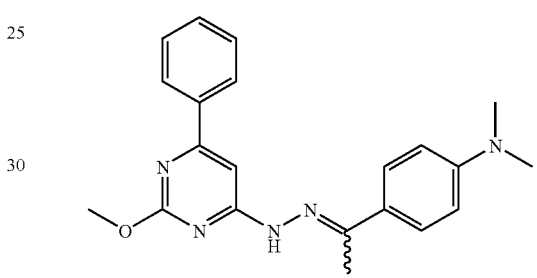

The title compound was prepared from (4-{1-[(6-chloro-2-methoxy-pyrimidin-4-yl)hydrazono]-ethyl}-phenyl)-dimethylamine (100 mg, 0.31 mmol), phenyl boronic acid (190 mg, 1.6 mmol), 1,3-bis(2,4,6-trimethylphenyl)imidazolium chloride (15 mg, 0.04 mmol), tris(dibenzylideneacetone)dipalladium (20 mg, 0.02 mmol) and cesium carbonate (611 mg, 1.9 mmol) in 1,4-dioxane (3 mL) by a procedure similar to Example 9, Step 3 yielding 61 mg (54%) of a yellow solid. HPLC Purity: 92%.

LCMS: Mass found (M+1, 362; M+Na, 384), $^1$H NMR: (CD$_3$OD, 400 MHz) δ 11.09 (s, 1H), 8.91 (m, 1H), 8.53 (d, J=8.97 Hz, 2H), 8.32 (m, 3H), 8.11 (s, 1H), 7.54 (d, J=8.97 Hz, 2H), 4.13 (s, 3H), 3.75 (s, 6H), 3.08 (s, 3H).

Example 16

[4-(1{[2-Ethyl-6-(2-methoxy-phenyl)-pyrimidin-4-yl]-hydrazono}-ethyl)-phenyl]-dimethylamine Step 1: 2-Ethyl-6-(2-methoxy-phenyl)-3H-pyrimidin-4-one

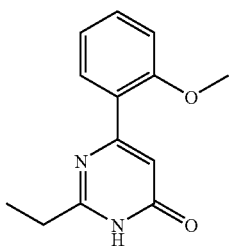

To a refluxing solution of saturated ammonium hydroxide (3 mL) in ethanol saturated with ammonia (3 mL) was added dropwise a solution of ethyl 2-methoxy benzoyl acetate (4.4 mL, 23 mmol) and triethyl orthopropionate (9.0 mL, 45 mmol) in 10 mL of ethanol. Ammonia gas was bubbled through the resultant reaction mixture throughout the entire timecourse of the reaction. The reaction mixture was refluxed overnight. The reaction was allowed to cool to room temperature and was concentrated in vacuo to approximately one third the original reaction volume. The concentrate was chilled and acetone was added, the resultant white solid was collected by vacuum filtration to yield 1.1 g (22%) of the title compound.

$^1$H NMR: (CD$_3$OD, 400 MHz) $\delta$7.87 (brs, 1H), 7.43 (m, 1H), 7.11 (d, J=8.06 Hz, 1H), 7.03 (t, J=8.06 Hz, 1H), 6.87 (brs, 1H), 3.89 (s, 3H), 2.68 (q, J=7.50 Hz, 2H), 1.33 (t, J=7.50 Hz, 3H).

Step 2: 4-Chloro-2-ethyl-6-(2-methoxy-phenyl)pyrimidine

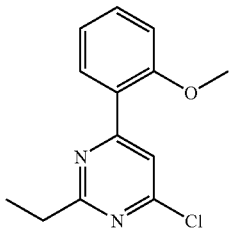

A solution of 2-ethyl-6-(2-methoxy-phenyl)-3H-pyrimidin-4-one (1.1 g, 4.9 mmol) and phosphorous oxychloride (3.0 mL, 32 mmol) was refluxed for four hours. After cooling to ambient temperature the reaction mixture was concentrated in vacuo and the resultant residue was diluted with dichloromethane. The organics were washed with ice-water. After extraction of the aqueous layer with dichloromethane the combined organics were washed with brine and dried over sodium sulfate. Following Si gel chromatography (1:5 ethyl acetate:hexanes) 0.91 g (74%) of the title compound was isolated as a pale yellow oil.

$^1$H NMR: (CDCl$_3$, 400 MHz) $\delta$ 8.07 (dd, J=1.84, 7.69 Hz, 1H), 7.83 (s, 1H), 7.45 (m, 1H), 7.09 (m, 1H), 7.00 (d, J=8.42 Hz, 1H), 3.91 (s, 3H), 3.00 (q, J=7.69 Hz, 2H), 1.40 (t, J=7.69 Hz, 3H).

Step 3: [4-(1{[2-Ethyl-6-(2-methoxy-phenyl)-pyrimidin-4-yl]-hydrazono}-ethyl)-phenyl]-dimethylamine

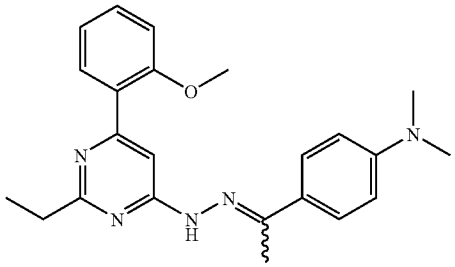

[2-Ethyl-6-(2-methoxy-phenyl)-pyrimidin-4-yl]-hydrazine was prepared from 4-chloro-2-ethyl-6-(2-methoxy-phenyl)pyrimidine (0.91 g, 3.7 mmol), hydrazine (0.69 mL, 22 mmol), sodium carbonate (0.76 g, 7.1 mmol) and potassium carbonate (0.79 g, 5.5 mmol) in dioxane (10 mL) by a procedure similar to example 3, step 1 yielding 0.77 g (86%) of a white solid.

A solution of [2-Ethyl-6-(2-methoxy-phenyl)-pyrimidin-4-yl]-hydrazine (100 mg, 0.41 mmol) and 4-dimethylaminoacetophenone (67 mg, 0.41 mmol) in ethanol (1.0 mL) was heated in the microwave (CEM Discover, 150 C, QuickTest method) for 6 hours. An initial purification by Si gel chromatography (2:1 hexanes:ethyl acetate) was followed by a crystallization from ethyl acetate:hexanes to yield 20 mg (13%) of the title compound as a yellow solid. HPLC Purity: 97%.

LCMS: Mass Found (M+1, 390), $^1$H NMR: (CDCl$_3$, 400 MHz) $\delta$ 7.92 (m, 1H), 7.72 (d, J=9.15 Hz, 2H), 7.40 (m, 1H), 7.07 (t, J=7.32 Hz, 1H), 7.01 (d, J=8.42 Hz, 1H), 6.71 (d, J=9.15 Hz, 2H), 3.92 (s, 3H), 3.00 (s, 6H), 2.86 (q, J=6.78 Hz, 2H), 3.18 (t, J=6.78 Hz, 3H).

Example 17

[4-(1-1{[6-(2-Methoxy-phenyl)-pyrimidin-4-yl]-hydrazono}-ethyl)-phenyl]dimethyl amine Step 1: 4-Chloro-6-(2-methoxy-phenyl)pyrimidine

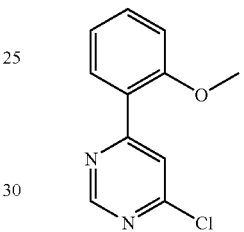

A solution of 4,6-dichloropyrimidine (2.0 g, 13 mmol), 2-methoxyphenylboronic acid (2.0 g, 13 mmol), and sodium carbonate (4.4 g, 42 mmol, dissolved in minimal amount of water) was degassed with argon. To the degassed solution Pd(Ph$_3$)$_4$ was added and the resultant reaction mixture was refluxed for 18 hours. The reaction mixture was cooled to room temperature and diluted with dichloromethane. The organics were washed with water and the aqueous layer was extracted with additional dichloromethane. The combined organics were washed with brine and dried over sodium sulfate. Following filtration, the organics were dried in vacuo and the residue was purified by Si gel chromatography (1:10 ethyl acetate:hexanes) to yield 2.4 g (80%) of the title compound.

1H NMR: (CDCl$_3$, 400 MHz) $\delta$ 9.02 (s, 1H), 8.05 (m, 2H), 7.47 (m, 2H), 7.10 (m, 1H), 7.02 (d, J=8.44 Hz, 1H), 3.93 (s, 3H).

Step 2: [4-(1-{[6-(2-Methoxy-phenyl)-pyrimidin-4-yl]-hydrazono}-ethyl)-phenyl]dimethyl amine

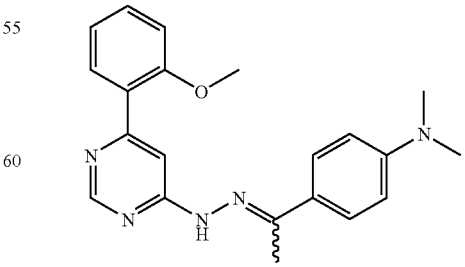

[6-(2-Methoxy-phenyl)-pyrimidin-4-yl]-hydrazine was prepared from 4-Chloro-6-(2-methoxy-phenyl)pyrimidine (2.4 g, 11 mmol), hydrazine (1.3 mL, 43 mmol) and potassium carbonate (2.2 g, 16 mmol) in 25 mL of dioxane by a procedure similar to example 3, step 1 yielding 2.0 g (86%) of a white solid.

[6-(2-Methoxy-phenyl)-pyrimidin-4-yl]-hydrazine (500 mg, 2.3 mmol) and 4-dimethylaminoacetophenone (380 mg, 2.3 mmol) were dissolved in 4 mL of ethanol. The resultant reaction mixture was heated in the microwave (CEM Discover, 135 C, QuickTest Method) for 3 hours. The reaction mixture was cooled to room temperature and after standing for three days yellow crystals formed. The crystalline solid was isolated by filtration and dried in vacuo to yield 580 mg (70%) of the title compound. HPLC Purity: 93%.

LCMS: (M+1, 362), $^1$H NMR: (CDCl$_3$, 400 MHz) δ 8.71 (s, 1H), 8.33 (s, 1H), 7.86-7.90 (m, 2H), 7.71 (d, J=8.97 Hz, 2H), 7.42 (m, 1H), 7.01-7.10 (m, 2H), 6.70 (d, J=8.97 Hz, 2H), 3.93 (s, 3H), 3.01 (s, 6H), 2.27 (s, 3H).

Example 18

Methyl-(4-{1-[(2-methyl-6-phenyl-pyrimidin-4-yl)-hydrazono]-ethyl}-phenyl)-amine Step 1: 4-Methylaminoacetophenone

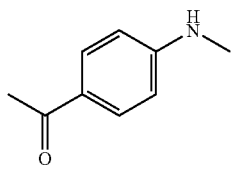

To a solution of 4-aminoacetophenone (1 g, 7.4 mmol) and methyl iodide (460 uL, 7.4 mmol) was added potassium tert-butoxide (1.7 g, 15 mmol) and the resultant reaction mixture was stirred overnight at room temperature. The reaction mixture was then diluted with dichloromethane and the organics were washed with water and brine. After concentrating the organics in vacuo, 400 mg (36%) of the title compound was isolated following Si gel chromatography.

1H NMR: (CDCl$_3$, 400 MHz) δ 7.83 (d, J=8.79 Hz, 2H), 6.59 (d, J=8.79 Hz, 2H), 2.90 (s, 3H), 2.50 (s, 3H).

Step 2: Methyl-(4-{1-[(2-methyl-6-phenyl-pyrimidin-4-yl)-hydrazono]-ethyl}-phenyl)-amine

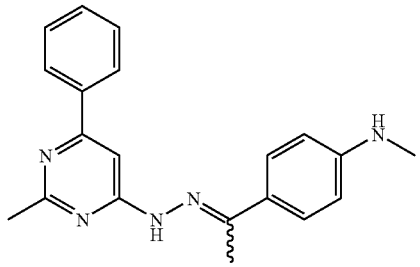

The title compound was prepared from 4-hydrazino-2-methyl-6-phenylpyrimidine trihydrochloride (300 mg, 0.97 mmol) and 4-methylaminoacetophenone (145 mg, 0.97 mmol) in ethanol (4.0 mL) by a procedure similar to example 1, step 4 yielding 62 mg (19%) of an orange solid. HPLC Purity: 91%.

LCMS: Mass found (M+1, 332), $^1$H NMR: (DMSO-d6, 400 MHz) δ 8.04 (brs, 2H), 7.85 (m, 2H), 7.67 (m, 3H), 7.42 (brs, 1H), 6.90 (brs, 2H), 2.74 (2 overlapping singlets, 6H), 2.40 (s, 3H).

Example 19

4-({1-[(2-Methyl-6-phenyl-pyrimidin-4-yl)-hydrazono]-ethyl}-phenyl)-thiourea

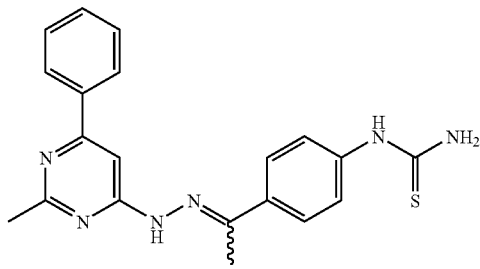

The title compound was prepared from 4-hydrazino-2-methyl-6-phenylpyrimidine trihydrochloride (300 mg, 0.97 mmol) and (4-acetyl-phenyl)-thiourea (188 mg, 0.97 mmol) in ethanol (4.0 mL) by a procedure similar to example 1, step 4 yielding 21 mg (6%) of a yellow solid. HPLC Purity: 92%.

LCMS: Mass found (M+1, 378), $^1$H NMR: (CDCl$_3$, 400 MHz) δ 8.42 (brs, 1H), 8.08 (m, 2H), 7.78 (d, J=8.60 Hz, 2H), 7.49 (m, 5H), 4.65 (brs, 2H), 2.63 (s, 3H), 2.27 (s, 3H).

Example 20

N-(4-{1-[(2-Methyl-6-phenyl-pyrimidin-4-yl)-hydrazono]-ethyl}-phenyl)-acetamide

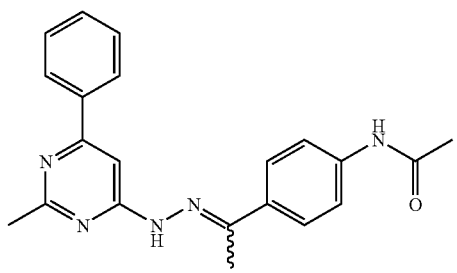

The title compound was prepared from 4-hydrazino-2-methyl-6-phenylpyrimidine trihydrochloride (300 mg, 0.97 mmol) and N-(4-acetyl-phenyl)acetamide (515 mg, 2.91 mmol) in ethanol (10.0 mL) by a procedure similar to example 1, step 4 yielding 43 mg (12%) of a brown solid. HPLC Purity: 95%.

LCMS: Mass Found (M+1, 360), $^1$H NMR: (DMSO-d6, 400 MHz) δ 10.42 (s, 1H), 7.4-8.1 (m, 10H), 2.71 (s, 3H), 2.44 (s, 3H).

Example 21

2-Methyl-4-{N'-[1-(4-methylamino-phenyl)-ethylidene]-hydrazino}-6-phenyl-pyrimidin-5-ylamine Step 1: 4-Chloro-2-mthyl-6-phenyl-pyrimidin-5-ylamine

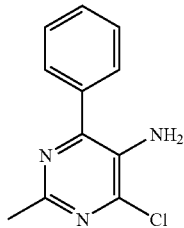

The title compound was prepared from 4,6-dichloro-2-methyl-pyrimidin-5-ylamine (500 mg, 2.8 mmol), phenylboronic acid (340 mg, 2.8 mmol), sodium carbonate (920 mg, 8.7 mmol, dissolved in minimal amount of water) and Pd(PPh$_3$)$_4$ (160 mg, 0.14 mmol) in 30 mL of glyme by a procedure similar to example 17, step 1 yielding 380 mg (61%) of a solid.

LCMS: Mass Found (M+1, 220.2), $^1$H NMR (CDCl$_3$, 400 MHz) δ 7.6-7.7 (m, 2H), 7.43-7.45 (m, 3H), 4.14 (brs, 2H), 2.59 (s, 3H).

Step 2: 2-Methyl-4-{N'-[1-(4-methylamino-phenyl)-ethylidene]-hydrazino}-6-phenyl-pyrimidin-5-ylamine

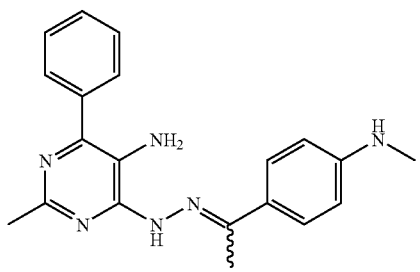

4-hydrazino-2-methyl-6-phenyl-pyrimidin-5-ylamine was prepared from 4-chloro-2-methyl-6-pyrimidin-5-ylamine (300 mg, 1.4 mmol), hydrazine (400 uL, 13 mmol) and potassium carbonate (580 mg, 4.2 mmol) in 3 mL of dioxane by a procedure similar to example 3, step 1 yielding 130 mg (44%, crude yield) of the hydrazine that was used directly in the subsequent condensation reaction.

The title compound was prepared from 4-hydrazino-2-methyl-6-phenyl-pyrimidin-5-ylamine (130 mg, 0.60 mmol) and 4-methylamineacetophenone (135 mg, 0.91 mmol) in 3.0 mL of ethanol by a procedure similar to example 1, step 4 yielding 92 mg (44%) of an orange solid. HPLC Purity: 91%.

LCMS: Mass Found (M+1, 347), $^1$H NMR: (DMSO-d6, 400 MHz) δ 7.2-8.0 (m, 7H), 6.56 (m, 2H), 6.03 (brs, 1H), 5.41 (brs, 1H), 1.21 (brs, 1H), 2.72 (s, 3H), 2.32 (m, 6H).

Example 22

N-(2-Methyl-6-phenyl-pyrimidin-4-yl)-N'-[1-p-tolyl-propylidene]-hydrazine

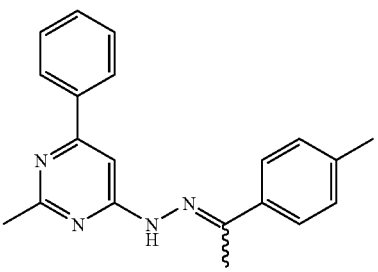

The title compound was prepared from 4-hydrazino-2-methyl-6-phenylpyrimidine (300 mg, 1.5 mmol) and 1-p-Tolyl-propan-1-one (174 μL, 1.05 mmol) in 3.0 mL of ethanol by a procedure similar to example 1, step 4 yielding 110 mg (22%) of a white solid. HPLC Purity: 96%.

LCMS: Mass Found (M+1, 331.1), $^1$H NMR: (CDCl$_3$, 400 MHz) δ8.16 (brs, 1H), 8.06 (m, 2H), 7.42-7.52 (m, 4H), 7.28 (d, 2H), 7.13 (d, 2H), 2.62 (q, 2H), 2.54 (s, 3H), 2.39 (s, 3H)

Example 23

N-[1-(4-Chloro-phenyl)ethylidene]-N'-(2-methyl-6-phenyl-pyrimidin-4-yl)-hydrazine

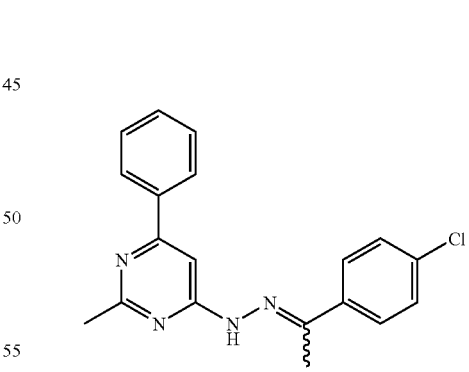

The title compound was prepared from 4-hydrazino-2-methyl-6-phenylpyrimidine (300 mg, 1.5 mmol) and 1-(4-Chloro-phenyl)-ethanone (136 μL, 1.05 mmol) in 8.0 mL of ethanol by a procedure similar to example 1, step 4 yielding 190 mg (38%) of an off-white solid. HPLC Purity: 98%.

LCMS: Mass Found: (M+1, 339.2, 337.1)

Example 24

N-[1-(4-Methoxy-phenyl)-ethylidene]-N'-(2-methyl-6-phenyl-pyrimidin-4-yl)-hydrazine

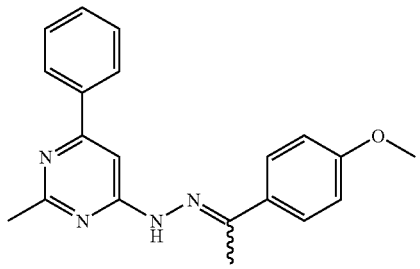

The title compound was prepared from 4-hydrazino-2-methyl-6-phenylpyrimidine (200 mg, 1.0 mmol) and 1-(4-methoxy-phenyl)-ethanone (150 mg, 1.0 mmol) in 10 mL of ethanol by a procedure similar to example 1, step 4 yielding 35 mg (11%) of a cream solid. HPLC Purity: 98%.

LCMS: Mass Found (M+1, 332.8), $^1$H NMR: (CD$_3$OD, 400 MHz) δ7.97 (m, 2H), 7.82 (d, 2H), 7.50 (m, 3H), 7.43 (s, 1H), 6.96 (d, 2H), 3.83 (s, 3H), 2.57 (s, 3H), 2.33 (s, 3H).

Example 25

N-[6-(2-Methoxy-phenyl)-pyrimidin-4-yl]-N'-[1-p-tolyl-ethylidene]-hydrazine

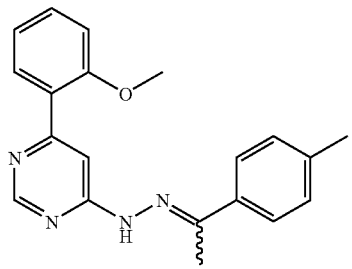

The title compound was prepared from [6-(2-methoxy-phenyl)-pyrimidin-4-yl]-hydrazine (500 mg, 2.3 mmol) and 4-methylacetophenone (310 μL, 2.3 mmol) in 10 mL of ethanol by a procedure similar to example 1, step 4 yielding 302 mg (39%) of a pale solid. HPLC Purity: 91%.

LCMS: Mass Found (M+1, 333.5), $^1$H NMR: (CDCl$_3$, 400 MHz) δ 8.76 (s, 1H), 8.46-8.56 (brs, 1H), 7.93 (m, 2H), 7.70 (d, 2H), 7.44 (t, 1H), 7.20 (d, 2H), 7.09 (t, 1H), 7.03 (d, 1H), 3.94 (s, 3H), 2.38 (s, 3H), 2.30 (s, 3H).

Example 26

N-[2-Ethyl-6-(2-methoxy-phenyl)-pyrimidin-4-yl]-N'-[1-p-tolyl-ethylidene]-hydrazine

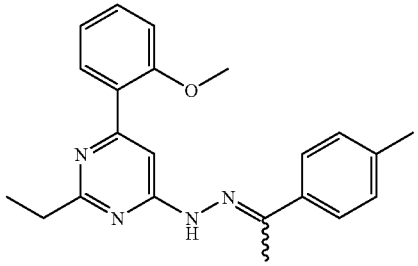

The title compound was prepared from [2-ethyl-6-(2-methoxy-phenyl)-pyrimidin-4-yl]-hydrazine (100 mg, 0.41 mmol) and 4-methylacetophenone (55 μL, 0.41 mmol) in 1.0 mL of ethanol by a procedure similar to example 1, step 4 yielding 117 mg (79%) of a yellow solid. HPLC Purity: 95%.

LCMS: Mass Found (M+1, 361.3), $^1$H NMR: (CDCl$_3$, 400 MHz) δ7.95 (m, 1H), 7.76 (s, 1H), 7.70 (d, 2H), 7.41 (m, 1H), 7.19 (d, 2H), 7.08 (m, 1H), 7.01 (d, 1H), 3.91 (s, 3H), 2.87 (q, 2H), 2.37 (s, 3H), 2.29 (s, 3H), 1.39 (t, 3H).

Example 27

N-[6-(2-Fluoro-phenyl)-2-methyl-pyrimidin-4-yl]-N'-[1-p-tolyl-ethylidene]-hydrazine Step-1: 4-Chloro-6-hydrazino-2-methylpyrimidine

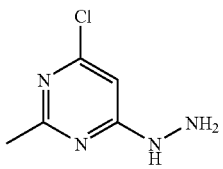

To a solution of 4,6-dichloro-2-methylpyrimidine (10 g, 0.061 mol) in dry THF (500 ml) was added anhydrous hydrazine (1.96 g, 0.061 mol) followed by potassium carbonate (12.7 g, 0.092 mol). The reaction mixture was stirred at room temperature for 13 h and filtered. The filtrate was evaporated under reduced pressure to afford 9.3 g (45%) of the titled compound as a solid.

LCMS: Mass found (M+1, 158.9), MP: Started melting at 146° C. and decomposed at 220° C., $^1$H NMR (CDCl$_3$, 300 MHz): δ 2.49 (3H, s), 3.05 (2H, bs), 6.59 (1H, bs), 6.67 (1H, s).

Step-2: (1)-1-(4-Methylphenyl)ethanone (6-chloro-2-methylpyrimidin-4-yl)hydrazone

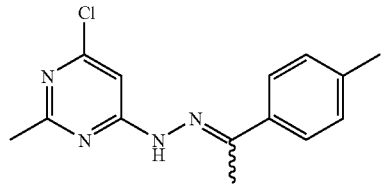

To a solution of 4-chloro-6-hydrazino-2-methylpyrimidine (9 g, 0.0567 mol) in dry toluene (200 ml) was added 4-methyl acetophenone (7.6 g, 0.056 mol) and the mixture was azeotropically refluxed under nitrogen for 16 h. The reaction mixture was cooled and the solvent was removed under reduced pressure. The residue was crystallized from pet ether/ethyl acetate to afford 9.8 g (63%) of the titled compound as a solid.

MP: 146-151° C., LCMS: Mass found (M+1, 275), $^1$H NMR (DMSO-d6, 300 MHz): δ 2.30 (3H, s), 2.32 (3H, s), 2.43 (3H, s), 7.02 (1H, s), 7.21-7.24 (1H, d, J=7.8 Hz), 7.71-7.74 (1H, d, J=7.8 Hz), 10.75 (1H, s).

Step 3: N-[6-(2-Fluoro-phenyl)-2-methyl-pyrimidin-4-yl]-N'-[1-p-tolyl-ethylidene]-hydrazine The title compound was prepared from (1)-1-(4-methylphenyl)ethanone (6-chloro-2-methylpyrimidin-4-yl)hydrazone (100 mg, 0.36 mmol), 2-fluorophenylboronic acid (255 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.2 mmol) in 1,4-dioxane (3 mL) by a procedure similar to Example 9, Step 3 yielding 81 mg (66%) of a yellow solid. HPLC Purity: 93%.

LCMS: Mass Found (M+1, 335.3). $^1$H NMR (CDCl$_3$, 400 MHz): δ 8.25 (brs, 1H), 8.02 (m, 1H), 7.67 (d, 2H), 7.60 (brs, 1H), 7.41 (m, 1H), 7.1-7.3 (m, 4H), 2.63 (s, 3H), 2.37 (s, 3H), 2.26 (s, 3H).

Example 28

N-[6-(3-Methoxy-phenyl)-2-methylpyrimidin-4-yl]-N'-[1-p-tolyl-ethylidene]-hydrazine

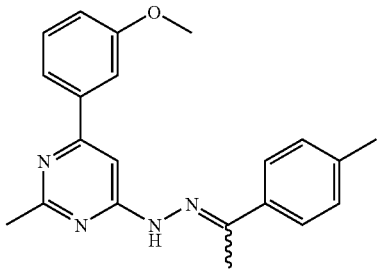

The title compound was prepared from (1)-1-(4-methylphenyl)ethanone (6-chloro-2-methylpyrimidin-4-yl)hydrazone (100 mg, 0.36 mmol), 3-methoxyphenylboronic acid (276 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.2 mmol) in 1,4-dioxane (3 mL) by a procedure similar to Example 9, Step 3 yielding 61 mg (48%) of a pale yellow solid. HPLC Purity: 96%.

LCMS: Mass Found (M+1, 347.2), $^1$H NMR (CDCl$_3$, 400 MHz): δ 8.25 (brs, 1H), 7.62-7.72 (m, 4H), 7.49 (s, 1H), 7.39 (m, 1H), 7.23 (m, 2H), 7.02 (m, 1H), 3.90 (s, 3H), 2.63 (s, 3H), 2.38 (s, 3H), 2.26 (s, 3H).

Example 29

N-[6-(2-Methoxy-phenyl)-2-methylpyrimidin-4-yl]-N'-[1-p-tolyl-ethylidene]-hydrazine

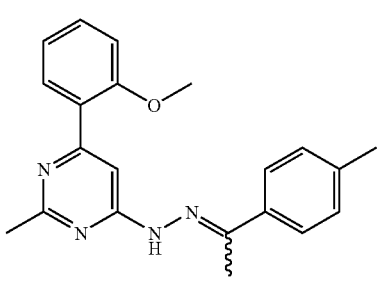

The title compound was prepared from (1)-1-(4-methylphenyl)ethanone (6-chloro-2-methylpyrimidin-4-yl)hydrazone (100 mg, 0.36 mmol), 2-methoxyphenylboronic acid (276 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.2 mmol) in 1,4-dioxane (3 mL) by a procedure similar to Example 9, Step 3 yielding 89 mg (70%) of a white solid. HPLC Purity: 91%.

LCMS: Mass Found (M+1, 347.3), $^1$H NMR (CDCl$_3$, 400 MHz): δ 8.23 (brs, 1H), 7.87 (d, 1H), 7.70 (m, 3H), 7.39 (m, 1H), 7.18 (d, 2H), 7.07 (t, 1H), 7.00 (d, 1H), 3.89 (s, 3H), 2.63 (s, 3H), 2.36 (s, 3H), 2.24 (s, 3H).

Example 30

N-[6-(4-Methoxy-phenyl)-2-methylpyrimidin-4-yl]-N'-[1-p-tolyl-ethylidene]-hydrazine

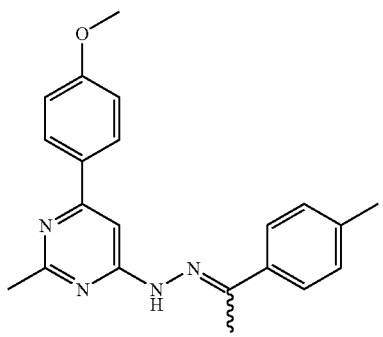

The title compound was prepared from (1)-1-(4-methylphenyl)ethanone (6-chloro-2-methylpyrimidin-4-yl)hydrazone (84 mg, 0.31 mmol), 4-methoxyphenylboronic acid (232 mg, 1.53 mmol), 1,3-bis(2,4,6-trimethylphenyl)imidazolium chloride (15 mg, 0.04 mmol), tris(dibenzylideneacetone)dipalladium (20 mg, 0.02 mmol) and cesium carbonate (598 mg, 1.83 mmol) in 1,4-dioxane (3 mL) by a procedure similar to Example 9, Step 3 yielding 70 mg (66%) of a white solid. HPLC Purity: 94%.

LCMS: Mass Found (M+1, 347.3).

Example 31

2-(2-Methyl-6-{N'-[1-p-tolyl-ethylidene]-hydrazino}-pyrimidin-4-yl)-benzonitrile

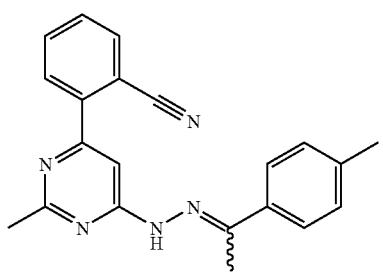

The title compound was prepared from (1)-1-(4-methylphenyl)ethanone (6-chloro-2-methylpyrimidin-4-yl)hydrazone (100 mg, 0.36 mmol), 2-cyanophenylboronic acid (267 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.2 mmol) in 1,4-dioxane (3 mL) by a procedure similar to Example 9, Step 3 yielding 37 mg (30%) of a pale yellow solid. HPLC Purity: 91%.

LCMS: Mass Found (M+1, 342.2), $^1$H NMR (CDCl$_3$, 400 MHz): δ 8.32 (brs, 1H), 7.89 (d, 1H), 7.70 (m, 3H), 7.52-7.56 (m, 2H), 7.20 (d, 2H), 2.65 (s, 3H), 2.36 (s, 3H), 2.28 (s, 3H).

Example 32

N-[6-(2-methyl-phenyl)-2-methyl-pyrimidin-4-yl]-N'-[1-p-tolyl-ethylidene]-hydrazine

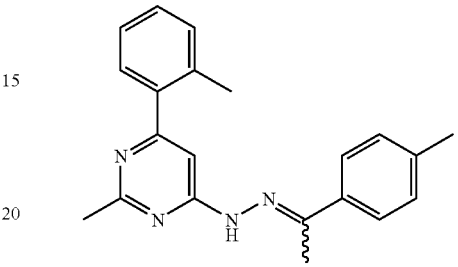

The title compound was prepared from (1)-1-(4-methylphenyl)ethanone (6-chloro-2-methylpyrimidin-4-yl)hydrazone (100 mg, 0.36 mmol), 2-methylphenylboronic acid (247 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.2 mmol) in 1,4-dioxane (3 mL) by a procedure similar to Example 9, Step 3 yielding 62 mg (52%) of a yellow solid. HPLC Purity: 91%.

LCMS: Mass Found (M+1, 331.1), $^1$H NMR (CDCl$_3$, 400 MHz): δ 8.25 (brs, 1H), 7.65 (d, 2H), 7.42 (m, 1H), 7.24-7.32 (m, 4H), 7.17 (d, 2H), 2.63 (s, 3H), 2.41 (s, 3H), 2.36 (s, 3H), 2.27 (s, 3H).

Example 33

N-[2-Methyl-6-(2-morpholin-4-yl-phenyl)-pyrimidin-4-yl]-N'-[1-p-tolyl-ethylidene]-hydrazine

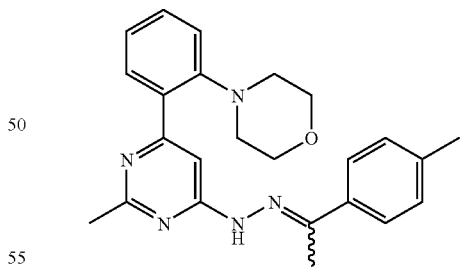

The title compound was prepared from (1)-1-(4-methylphenyl)ethanone (6-chloro-2-methylpyrimidin-4-yl)hydrazone (100 mg, 0.36 mmol), 2-morpholinophenylboronic acid (376 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.2 mmol) in 1,4-dioxane (3 mL) by a procedure similar to Example 9, Step 3 yielding 103 mg (70%) of a light brown solid. HPLC Purity: 95%.

LCMS: Mass Found (M+1, 402.2).

Example 34

N-[2-(2-Methyl-6-{N'-[1-p-tolyl-ethylidene]-hydrazino}-pyrimidin-4-yl)-phenyl]-acetamide

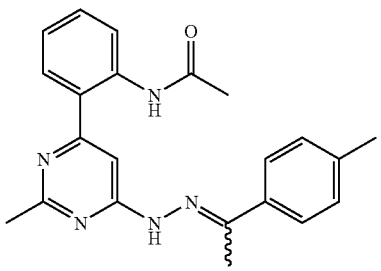

The title compound was prepared from (1)-1-(4-methylphenyl)ethanone (6-chloro-2-methylpyrimidin-4-yl)hydrazone (60 mg, 0.22 mmol), (2-acetylaminophenyl)boronic acid (195 mg, 1.09 mmol), 1,3-bis(2,4,6-trimethylphenyl)imidazolium chloride (10 mg, 0.03 mmol), tris(dibenzylideneacetone)dipalladium (14 mg, 0.02 mmol) and cesium carbonate (430 mg, 1.3 mmol) in 1,4-dioxane (2 mL) by a procedure similar to Example 9, Step 3 yielding 53 mg (65%) of a dark pink solid. HPLC Purity: 92%.

LCMS: Mass Found (M+1, 374.2), $^1$H NMR (CDCl$_3$, 400 MHz): δ 8.58 (d, 1H), 8.32 (brs, 1H), 7.80 (d, 1H), 7.69 (d, 2H), 7.40-7.49 (m, 3H), 7.1-7.3 (m, 4H), 2.64 (s, 3H), 2.39 (s, 3H), 2.30 (s, 3H), 2.20 (s, 3H).

Example 35

[2-(2-Methyl-6-{N'-[1-p-tolyl-ethylidene]-hydrazino}-pyrimidin-4-yl)-phenyl]-methanol

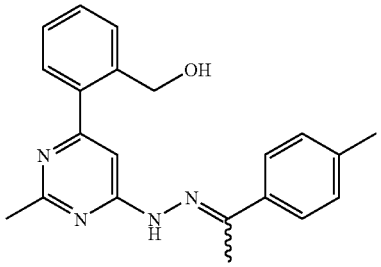

The title compound was prepared from (1)-1-(4-methylphenyl)ethanone (6-chloro-2-methylpyrimidin-4-yl)hydrazone (60 mg, 0.22 mmol), (hydroxymethylphenyl)boronic acid dehydrate (166 mg, 1.09 mmol), 1,3-bis(2,4,6-trimethylphenyl)imidazolium chloride (10 mg, 0.03 mmol), tris(dibenzylideneacetone)dipalladium (14 mg, 0.02 mmol) and cesium carbonate (430 mg, 1.3 mmol) in 1,4-dioxane (2 mL) by a procedure similar to Example 9, Step 3 yielding 55 mg (73%) of a light pink solid. HPLC Purity: 92%.

LCMS: Mass Found (M+1, 347.2), $^1$H NMR (CDCl$_3$, 400 MHz): δ 8.35 (brs, 1H), 7.67 (m, 3H), 7.42-7.50 (m, 4H), 7.37 (s, 1H), 7.21 (d, 2H), 4.50 (s, 2H), 2.61 (s, 3H), 2.37 (s, 3H), 2.29 (s, 3H).

Example 36

N-[6-(3,5-Dimethyl-isoxazol-4-yl)-2-methyl-pyrimidin-4-yl]-N'-[1-p-tolyl-ethylidene]-hydrazine

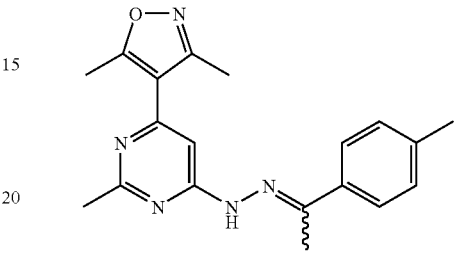

The title compound was prepared from (1)-1-(4-methylphenyl)ethanone (6-chloro-2-methylpyrimidin-4-yl)hydrazone (100 mg, 0.36 mmol), 3,5-dimethylisoxazole-4-boronic acid (154 mg, 1.09 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (427 mg, 1.3 mmol) in 1,4-dioxane (4 mL) by a procedure similar to Example 9, Step 3 yielding 30 mg (24%) of a white solid. HPLC Purity: 98%.

LCMS: Mass Found (M+1, 336.2), $^1$H NMR (CDCl$_3$, 400 MHz): δ 8.30 (brs, 1H), 7.65 (d, 2H), 7.21 (d, 2H), 7.16 (s, 1H), 2.66 (s, 3H), 2.58 (s, 3H), 2.49 (s, 3H), 2.38 (s, 3H), 2.27 (s, 3H).

Example 37

N-(2-Methyl-6-pyridin-3-yl-pyrimidin-4-yl)-N'-[1-p-tolyl-ethylidene]-hydrazine

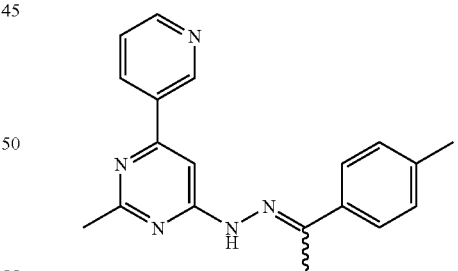

The title compound was prepared from (1)-1-(4-methylphenyl)ethanone (6-chloro-2-methylpyrimidin-4-yl)hydrazone (100 mg, 0.36 mmol), pyridine-3-boronic acid (134 mg, 1.09 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (427 mg, 1.3 mmol) in 1,4-dioxane (3 mL) by a procedure similar to Example 9, Step 3 yielding 16 mg (14%) of a light brown solid. HPLC Purity: 91%.

LCMS: Mass Found (M+1, 318.0), $^1$H NMR (CDCl$_3$, 400 MHz): δ 9.27 (m, 1H), 8.70 (m, 1H), 8.38 (m, 1H), 8.28 (brs, 1H), 7.69 (m, 2H), 7.54 (s, 1H), 7.41 (m, 1H), 7.21 (m, 2H), 2.63 (s, 3H), 2.39 (s, 3H), 2.29 (s, 3H).

Example 38

2-(2-Methyl-6-{N'-[1-p-tolyl-ethylidene]-hydrazino}-pyrimidin-4-yl)-phenylamine

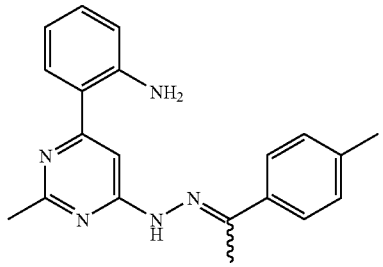

The title compound was prepared from (1)-1-(4-methylphenyl)ethanone (6-chloro-2-methylpyrimidin-4-yl)hydrazone (130 mg, 0.47 mmol), (2-BOC-aminophenyl)boronic acid (560 mg, 2.37 mmol), 1,3-bis(2,4,6-trimethylphenyl)imidazolium chloride (23 mg, 0.07 mmol), tris(dibenzylideneacetone)dipalladium (30 mg, 0.03 mmol) and cesium carbonate (925 mg, 2.8 mmol) in 1,4-dioxane (4 mL) by a procedure similar to Example 9, Step 3 yielding 16 mg (10%) of a white solid. HPLC Purity: 95%. (Reaction also yielded 106 mg (52%) of [2-(2-Methyl-6-{N'-[1-p-tolyl-ethylidene]-hydrazino}-pyrimidin-4-yl)-phenyl]-carbamic acid tert-butyl ester).

LCMS: Mass Found (M+1, 332.2.0), $^1$H NMR (CDCl$_3$, 400 MHz): δ 8.19 (brs, 1H), 7.69 (d, 2H), 7.66 (d, 1H), 7.42 (s, 1H), 7.16-7.24 (m, 3H), 6.78 (t, 1H), 6.72 (d, 1H), 5.92 (brs, 2H), 2.59 (s, 3H), 2.38 (s, 3H), 2.27 (s, 3H).

Example 39

N-Methyl-N-(2-methyl-6-phenyl-pyrimidin-4-yl)-N'-[1-p-tolyl-ethylidene]-hydrazine

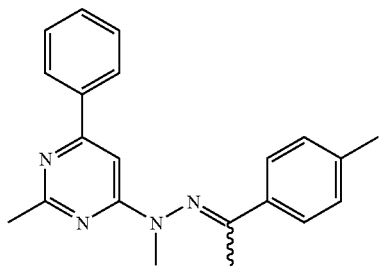

N-methyl-N-(2-methyl-6-phenyl-pyrimidin-4-yl)-hydrazine was prepared from 4-chloro-2-methyl-6-phenylpyrimidine (500 mg, 2.4 mmol), methylhydrazine (0.52 mL, 9.8 mmol) and potassium carbonate (506 mg, 3.7 mmol) in 5 mL of 1,4 dioxane by a procedure similar to example 3, step 1 yielding 392 mg (75%) of a pale yellow solid.

The title compound was prepared from N-methyl-N-(2-methyl-6-phenyl-pyrimidin-4-yl)-hydrazine (196 mg, 0.91 mmol) and 4-methylacetophenone (122 μL, 0.91 mmol) in 10 mL of ethanol by a procedure similar to example 8, step 4 yielding 180 mg (60%) of a cream solid. HPLC Purity: 97%.

LCMS: Mass Found (M+1, 331.4), $^1$H NMR (CDCl$_3$, 400 MHz): δ 7.94 (m, 2H), 7.86 (d, 2H), 7.41 (m, 3H), 7.27 (d, 2H), 6.84 (s, 1H), 3.43 (s, 3H), 2.68 (s, 3H), 2.42 (s, 3H), 2.38 (s, 3H).

Example 40

N-[6-(2,6-Dimethoxy-phenyl)-2-methyl-pyrimidin-4-yl]-N'-[1-p-tolyl-ethylidene]-hydrazine

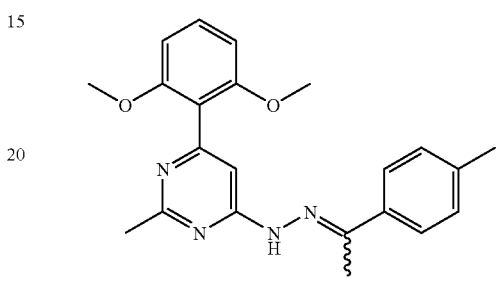

The title compound was prepared from (1)-1-(4-methylphenyl)ethanone (6-chloro-2-methylpyrimidin-4-yl)hydrazone (100 mg, 0.36 mmol), 2,6-dimethoxyphenyl-boronic acid (331 mg, 1.82 mmol), 1,3-bis(2,4,6-trimethylphenyl)imidazolium chloride (17 mg, 0.05 mmol), tris(dibenzylideneacetone)dipalladium (23 mg, 0.03 mmol) and cesium carbonate (711 mg, 2.18 mmol) in 1,4-dioxane (3 mL) by a procedure similar to Example 9, Step 3 yielding 54 mg (39%) of a light yellow solid. HPLC Purity: 98%.

LCMS: Mass Found (M+1, 377.2), $^1$H NMR (CDCl$_3$, 400 MHz): δ 8.21 (brs, 1H), 7.65 (d, 2H), 7.16-7.12 (m, 3H), 3.73 (s, 6H), 2.62 (s, 3H), 2.34 (s, 3H), 2.24 (s, 3H).

Example 41

Preparation of a Pharmaceutical Formulation

The following formulation examples illustrate representative pharmaceutical compositions according to the present invention being not restricted thereto.

Formulation 1—Tablets

A compound of Formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound compound per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active compound per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 ml.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5—Injection

A compound of Formula (I) is dissolved in a buffered sterile saline injectable aqueous medium to a concentration of approximately 5 mg/ml.

Biological Assays

Assay 1: Tumor Cell Proliferation Assay:

Colon cancer (C26, murine), pancreatic cancer (MiaPaCa-2, human) cells were plated in 96-well white plates (Cat. No. 3917, Corning, Inc.) at $2.5 \times 10^3$ cells/well and cultured overnight at 37° C. in 5% CO2 in DMEM containing 10% FCS. Inhibitors were serially diluted in 100% DMSO and subsequently added to cells to reach a final concentration of 0.25% DMSO. Cell plates were incubated for an additional 4 days at 37° C. and 5% CO2 and cell proliferation was quantitated using the ATP-lite cell proliferation kit (Cat. No. 6016943, Perkin Elmer).

The ATPlite kit quantifies the ATP released from lysed cells by the generation of light caused by the reaction of the released ATP with the Luciferase and D-Luciferin contained in the kit. After the 4$^{th}$ day of incubation, the media is removed from the cell plates and replaced with 100 μL of PBS followed by 50 μL of the lysis solution. The plates are then shaken for 5 minutes on an orbital shaker followed by the addition of 50 μL of substrate solution. The plates are shaken for an additional 5 minutes followed by dark adaptation for 10 minutes and finally read on a Victor$^3$ V plate reader (1 second/well, Cat. No. 1420-041, Perkin Elmer).

Inhibition of cell proliferation is shown in Table 1. Columns 2-3 show the concentration of compounds required to inhibit the growth of tumor cells by 50% (IC50 in μM). With "+" meaning 1 μM<IC50<15 μM and "++" IC50<1 μM and "n.d." means not determined.

TABLE 1

Inhibition of tumor cell proliferation

| Compound no. | C26 IC$_{50}$ [μM] | MiaPaCa-2 IC$_{50}$ [μM] |
|---|---|---|
| 1 | ++ | ++ |
| 2 | ++ | ++ |
| 3 | + | + |
| 4 | + | + |
| 5 | + | + |
| 6 | + | + |
| 7 | ++ | ++ |
| 8 | ++ | ++ |
| 9 | ++ | ++ |
| 10 | ++ | ++ |
| 11 | ++ | ++ |
| 12 | + | ++ |
| 13 | ++ | ++ |
| 14 | ++ | ++ |
| 15 | ++ | ++ |
| 16 | ++ | ++ |
| 17 | ++ | ++ |
| 18 | ++ | ++ |
| 19 | + | + |
| 20 | + | + |
| 21 | ++ | ++ |
| 22 | + | + |
| 23 | + | n.d. |
| 24 | ++ | n.d. |
| 25 | ++ | ++ |
| 26 | ++ | ++ |
| 27 | ++ | ++ |
| 28 | | + |
| 29 | ++ | ++ |
| 30 | | + |
| 31 | ++ | ++ |
| 32 | ++ | ++ |
| 33 | + | ++ |
| 34 | ++ | ++ |
| 35 | ++ | ++ |
| 36 | ++ | ++ |
| 37 | + | n.d. |
| 38 | ++ | ++ |
| 39 | ++ | ++ |
| 40 | ++ | ++ |
| 41 | ++ | ++ |
| 42 | + | + |
| 43 | ++ | n.d. |
| 44 | + | n.d. |
| 45 | + | n.d. |
| 46 | + | n.d. |
| 47 | + | n.d. |
| 48 | + | n.d. |

Assay 2: Endothelial Tube Formation Assay

Human umbilical vein endothelial cells (HUVEC) (Cascade Biologics #C-003-5C) were plated into 96-well black clear-bottom microplates (Cat. No. 3603, Corning, Inc.) containing 50 uL/well of BD Matrigel Basement Membrane Matrix (BD Biosciences #354234) at $7.5 \times 10^3$ cells/well. Inhibitors were serially diluted in 100% DMSO and subsequently added to cells to reach a final concentration of 0.5% DMSO and the plates cultured overnight at 37° C., 5% CO2 in (EGM™-2 MV) (Cambrex #CC-3202). After the incubation, the assay medium was removed and the cell plates washed once with Hank's Balance Salt Solution (HBSS) (Invitrogen #24020-117) followed by the addition of 50 μl of 8 μg/ml Calcein AM (Molecular Probes #C1430) in HBSS to each well. Cell plates were incubated in the dark at 37° C., 5% $CO_2$ for 10 minutes and then immediately imaged and quantitated on the Discovery—1 automated microscope (Molecular Devices Corp.) to determine the total endothelial tube length. The total endothelial tube length is calculated using the Angiogenesis image algorithm supplied with the MetaMorph software package (Molecular Devices Corp). In short, a fluorescent image of a given well is captured by exciting the well using 488 nm excitation light and collecting the fluorescent image using a 530 nm emission bandpass filter. The image is then thresholded to identify the fluorescent endothelial tubes and then reduced to a binary image, pixels above the threshold are given a value of 1 while pixels below the threshold are given a value of 0. The binary image is then analyzed to remove objects that are not part of the endothelial tube network, such as cell clumps or debris. Finally, the corrected binary image is processed to reduce the tubes to single pixel width from which the total tube length is calculated. The total endothelial tube length data for a given sample is then converted to percent inhibition by subtracting the value from the total tube length of the DMSO-treated control wells and then dividing by the total tube length of the DMSO-treated control wells. The IC50 is equal to the concentration at which there is a 50% reduction in total endothelial tube length.

Wherein "++" means an IC50<1 µM

TABLE 2

Tube Formation (HUVEC)

| Compound No | IC$_{50}$ (µM) |
|---|---|
| 2 | ++ |
| 7 | ++ |

Assay 3: Tumor Inhibition Isograft Study 5 week old male CD2F1 mice (22-24 g each, Charles River Laboratories) are subcutaneously injected with 1.5 million Colon cancer cells (C26, murine) in the back. The tumors are grown for 7 days in the mice in order to reach a size of 200 mm$^3$ at which point they are sorted and separated into 4 groups of seven mice each for the following treatments; 1) sesame oil vehicle by p. os bid, 2) 10 mg/kg of a compound of Formula (I) in sesame oil by p. os bid, 3) 30 mg/kg of a compound of Formula (I) in sesame oil by p. os bid, 4) of a compound of Formula (I) 100 mg/kg in sesame oil by p. os bid. Starting on day 8, the mice are gavaged with their respective treatment for 14 days or until their tumors are >2000 mm$^3$ or the animals are moribund. On days 2, 5, 7, 9, 12 and 14, the tumors are measured through the skin with calipers to determine the tumor volume and the mice are weighed to determine body weight change. On day 14 the animals are sacrificed and the tumors removed, weighed and flash frozen for histology follow-up.

Reference List

Schreiber, S. L., *Chemical and Engineering News* 81 (2003): 51-61

DePalma, A. Drug Discovery and Development 7 (2004): 51

The invention claimed is:

1. A compound selected from the group consisting of:
   N-Methyl-N'-(1-m-tolyl-ethylidene)-N-(2-trifluoromethylquinazolin-4-yl)-hydrazine;
   N-Methyl-N'-(1-p-tolyl-ethylidene)-N-(2-trifluoromethylquinazolin-4-yl)-hydrazine;
   N-(1-p-Tolyl-ethylidene)-N'-(2-trifluoromethyl-quinazolin-4-yl)-hydrazine;
   N-[1-(4-methoxy-phenyl)-ethylidene]-N'-(2-methyl-quinazolin-4-yl)-hydrazine;
   N-(2-Methyl-quinazolin-4-yl)-N-(1-p-tolyl-ethylidene)-hydrazine;
   N-(2-methyl-quinazolin-4-yl)-N'-(1-m-tolyl-ethylidene)-hydrazine;
   N-Methyl-N-(2-methyl-quinazolin-4-yl)-N-(1-p-tolyl-ethylidene)-hydrazine;
   Dimethyl-(4-{1-[(2-methyl-6-phenyl-pyrimidin-4-yl)-hydrazono]ethyl}-phenyl) amine;
   [4-(1-{[6-(2-Methoxy-phenyl)-2-methyl-pyrimidin-4-yl]-hydrazono}-ethyl)-phenyl]-dimethylamine;
   [4-(1-{[6-(3,5-dimethyl-isoxazol-4-yl)-2-methyl-pyrimidin-4-yl]-hydrazono}-ethyl)-phenyl]-dimethylamine;
   Dimethyl-[4-(1-{[2-methyl-6-(2-trifluoromethoxy-phenyl)-pyrimidin-4-yl]-hydrazono}-ethyl)-phenyl]-amine;
   [4-(1-{[6-(2-Isopropoxy-phenyl)-2-methyl-pyrimidin-4-yl]-hydrazono}-ethyl)-phenyl]-dimethylamine;
   [4-(1-{[6-(2-Fluoro-phenyl)-2-methyl-pyrimidin-4-yl]-hydrazono}-ethyl)-phenyl]-dimethylamine;
   [4-(1-{[6-(2-amino-phenyl)-2-methyl-pyrimidin-4-yl]-hydrazono}-ethyl)-phenyl]-dimethylamine;
   (4-{1-[(2-Methoxy-6-phenyl-pyrimidin-4-yl)-hydrazono]-ethyl}-phenyl)-dimethylamine;
   [4-(1{[2-Ethyl-6-(2-methoxy-phenyl)-pyrimidin-4-yl]-hydrazono}-ethyl)-phenyl]dimethylamine;
   [4-(1-{[6-(2-Methoxy-phenyl)-pyrimidin-4-yl]-hydrazono}-ethyl)-phenyl] dimethyl amine;
   Methyl-(4-{1-[(2-methyl-6-phenyl-pyrimidin-4-yl)-hydrazono]-ethyl}-phenyl)-amine;
   4-({1-[(2-Methyl-6-phenyl-pyrimidin-4-yl)-hydrazono]-ethyl}-phenyl)-thiourea;
   N-(4-{1-[(2-Methyl-6-phenyl-pyrimidin-4-yl)-hydrazono]-ethyl}-phenyl)-acetamide;
   2-Methyl-4-{N'-[1-(4-methylamino-phenyl)-ethylidene]-hydrazino}-6-phenyl-pyrimidin-5-ylamine;
   N-(2-Methyl-6-phenyl-pyrimidin-4-yl)-N'-[1-p-tolyl-propylidene]-hydrazine;
   N-[1-(4-Chloro-phenyl)ethylidene]-N'-(2-methyl-6-phenyl-pyrimidin-4-yl)-hydrazine;
   N-[1-(4-Methoxy-phenyl)-ethylidene]-N'-(2-methyl-6-phenyl-pyrimidin-4-yl)-hydrazine;
   N-[6-(2-Methoxy-phenyl)-pyrimidin-4-yl]-N'-[1-p-tolyl-ethylidene]-hydrazine;
   N-[2-Ethyl-6-(2-methoxy-phenyl)-pyrimidin-4-yl]-N'-[1-p-tolyl-ethylidene]-hydrazine;
   N-[6-(2-Fluoro-phenyl)-2-methyl-pyrimidin-4-yl]-N'-[1-p-tolyl-ethylidene]-hydrazine;
   N-[6-(3-Methoxy-phenyl)-2-methyl pyrimidin-4-yl]-N'-[1-p-tolyl-ethylidene]-hydrazine
   N-[6-(2-Methoxy-phenyl)-2-methyl pyrimidin-4-yl]-N'-[1-p-tolyl-ethylidene]-hydrazine;
   N-[6-(4-Methoxy-phenyl)-2-methyl pyrimidin-4-yl]-N'-[1-p-tolyl-ethylidene]-hydrazine;
   2-(2-Methyl-6-{N'-[1-p-tolyl-ethylidene]-hydrazino}-pyrimidin-4-yl)-benzonitrile;
   N-[6-(2-methyl-phenyl)-2-methyl-pyrimidin-4-yl]-N'-[1-p-tolyl-ethylidene]-hydrazine;
   N-[2-Methyl-6-(2-morpholin-4-yl-phenyl)-pyrimidin-4-yl]-N'[1-p-tolyl-ethylidene]-hydrazine;
   N-[2-(2-Methyl-6-{N'-[1-p-tolyl-ethylidene]-hydrazino}-pyrimidin-4-yl)-phenyl]-acetamide;
   [2-(2-Methyl-6-{N'-[1-p-tolyl-ethylidene]-hydrazino}-pyrimidin-4-yl)-phenyl]-methanol;
   N-[6-(3,5-Dimethyl-isoxazol-4-yl)-2-methyl-pyrimidin-4-yl]-N'[1-p-tolyl-ethylidene]-hydrazine;
   N-(2-Methyl-6-pyridin-3-yl-pyrimidin-4-yl)-N'-[1-p-tolyl-ethylidene]-hydrazine;
   2-(2-Methyl-6-{N'-[1-p-tolyl-ethylidene]-hydrazino}-pyrimidin-4-yl)-phenylamine;
   N-Methyl-N-(2-methyl-6-phenyl-pyrimidin-4-yl)-N'-[1-p-tolyl-ethylidene]-hydrazine; and
   N-[6-(2,6-Dimethoxy-phenyl)-2-methyl-pyrimidin-4-yl]-N'-[1-p-tolyl-ethylidene]-hydrazine.

2. A pharmaceutical composition comprising a pharmaceutically acceptable carrier, diluent or excipient thereof and at least one compound selected from the group consisting of:
   N-Methyl-N'-(1-m-tolyl-ethylidene)-N-(2-trifluoromethylquinazolin-4-yl)-hydrazine;
   N-Methyl-N'-(1-p-tolyl-ethylidene)-N-(2-trifluoromethylquinazolin-4-yl)-hydrazine;
   N-(1-p-Tolyl-ethylidene)-N'-(2-trifluoromethyl-quinazolin-4-yl)-hydrazine;
   N-[1-(4-methoxy-phenyl)-ethylidene]-N'-(2-methyl-quinazolin-4-yl)-hydrazine;
   N-(2-Methyl-quinazolin-4-yl)-N-(1-p-tolyl-ethylidene)-hydrazine;
   N-(2-methyl-quinazolin-4-yl)-N'-(1-m-tolyl-ethylidene)-hydrazine;
   N-Methyl-N-(2-methyl-quinazolin-4-yl)-N-(1-p-tolyl-ethylidene)-hydrazine;

Dimethyl-(4-{1-[(2-methyl-6-phenyl-pyrimidin-4-yl)-hydrazono]ethyl}-phenyl) amine;
[4-(1-{[6-(2-Methoxy-phenyl)-2-methyl-pyrimidin-4-yl]-hydrazono}-ethyl)-phenyl]-dimethylamine;
[4-(1-{[6-(3,5-dimethyl-isoxazol-4-yl)-2-methyl-pyrimidin-4-yl]-hydrazono}-ethyl)-phenyl]-dimethylamine;
Dimethyl-[4-(1-{[2-methyl-6-(2-trifluoromethoxy-phenyl)-pyrimidin-4-yl]-hydrazono}-ethyl)-phenyl]-amine;
[4-(1-{[6-(2-Isopropoxy-phenyl)-2-methyl-pyrimidin-4-yl]-hydrazono}-ethyl)-phenyl]-dimethylamine;
[4-(1-{[6-(2-Fluoro-phenyl)-2-methyl-pyrimidin-4-yl]-hydrazono}-ethyl)-phenyl]-dimethylamine;
[4-(1-{[6-(2-amino-phenyl)-2-methyl-pyrimidin-4-yl]-hydrazono}-ethyl)-pheny]-dimethylamine;
(4-{1-[(2-Methoxy-6-phenyl-pyrimidin-4-yl)-hydrazono]-ethyl}-phenyl)-dimethylamine;
[4-(1{[2-Ethyl-6-(2-methoxy-phenyl)-pyrimidin-4-yl]-hydrazono}-ethyl)-phenyl]-dimethylamine;
[4-(1-{[6-(2-Methoxy-phenyl)-pyrimidin-4-yl]-hydrazono}-ethyl)-phenyl]dimethyl amine;
Methyl-(4-{1-[(2-methyl-6-phenyl-pyrimidin-4-yl)-hydrazono]-ethyl}-phenyl)-amine;
4-({1-[(2-Methyl-6-phenyl-pyrimidin-4-yl)-hydrazono]-ethyl}-phenyl)-thiourea;
N-(4-{1-[(2-Methyl-6-phenyl-pyrimidin-4-yl)-hydrazono]-ethyl}-phenyl)-acetamide;
2-Methyl-4-{N'-[1-(4-methylamino-phenyl)-ethylidene]-hydrazino}-6-phenyl-pyrimidin-5-ylamine;
N-(2-Methyl-6-phenyl-pyrimidin-4-yl)-N'-[1-p-tolyl-propylidene]-hydrazine;
N-[1-(4-Chloro-phenyl)ethylidene]-N'-(2-methyl-6-phenyl-pyrimidin-4-yl)-hydrazine;
N-[1-(4-Methoxy-phenyl)-ethylidene]-N'-(2-methyl-6-phenyl-pyrimidin-4-yl)-hydrazine;
N-[6-(2-Methoxy-phenyl)-pyrimidin-4-yl]-N'-[1-p-tolyl-ethylidene]-hydrazine;
N-[2-Ethyl-6-(2-methoxy-phenyl)-pyrimidin-4-yl]-N'-[1-p-tolyl-ethylidene]-hydrazine;
N-[6-(2-Fluoro-phenyl)-2-methyl-pyrimidin-4-yl]-N'-[1-p-tolyl-ethylidene]-hydrazine;
N-[6-(3-Methoxy-phenyl)-2-methyl pyrimidin-4-yl]-N'-[1-p-tolyl-ethylidene]-hydrazine
N-[6-(2-Methoxy-phenyl)-2-methyl pyrimidin-4-yl]-N'-[1-p-tolyl-ethylidene]-hydrazine;
N-[6-(4-Methoxy-phenyl)-2-methyl pyrimidin-4-yl]-N'-[1-p-tolyl-ethylidene]-hydrazine;
2-(2-Methyl-6-{N'-[1-p-tolyl-ethylidene]-hydrazino}-pyrimidin-4-yl)-benzonitrile;
N-[6-(2-methyl-phenyl)-2-methyl-pyrimidin-4-yl]-N'-[1-p-tolyl-ethylidene ]-hydrazine;
N-[2-Methyl-6-(2-morpholin-4-yl-phenyl)-pyrimidin-4-yl]-N'-[1-p-tolyl-ethylidene]-hydrazine;
N-[2-(2-Methyl-6-{N'-[1-p-tolyl-ethylidene]-hydrazino}-pyrimidin-4-yl)-phenyl]-acetamide;
[2-(2-Methyl-6-{N'-[1-p-tolyl-ethylidene]-hydrazino}-pyrimidin-4-yl)-phenyl]-methanol;
N-[6-(3,5-Dimethyl-isoxazol-4-yl)-2-methyl-pyrimidin-4-yl]-N'-[1-p-tolyl-ethylidene]-hydrazine;
N-(2-Methyl-6-pyridin-3-yl-pyrimidin-4-yl)-N'-[1-p-tolyl-ethylidene]-hydrazine;
2-(2-Methyl-6-{N'-[1-p-tolyl-ethylidene]-hydrazino}-pyrimidin-4-yl)-phenylamine;
N-Methyl-N-(2-methyl-6-phenyl-pyrimidin-4-yl)-N'-[1-p-tolyl-ethylidene]-hydrazine; and
N-[6-(2,6-Dimethoxy-phenyl)-2-methyl-pyrimidin-4-yl]-N'-[1-p-tolyl-ethylidene]-hydrazine.

\* \* \* \* \*